United States Patent [19]

Ochiai et al.

[11] 4,278,671
[45] Jul. 14, 1981

[54] 7-[2-(2-AMINOTHIAZOL-4-yL)-2-(SYN)-METHOXYIMINOACETAMIDO] CEPHALOSPORINS

[75] Inventors: Michihiko Ochiai, Suita; Akira Morimoto, Ikeda; Yoshihiro Matsushita, Nishinomiya, all of Japan

[73] Assignee: Takeda Chemical Industries, Ltd., Osaka, Japan

[21] Appl. No.: 64,743

[22] Filed: Aug. 8, 1979

Related U.S. Application Data

[63] Continuation of Ser. No. 787,258, Apr. 13, 1977, abandoned.

[30] Foreign Application Priority Data

Apr. 14, 1976 [JP] Japan .................................. 51-42885
Sep. 8, 1976 [JP] Japan .................................. 51-108102

[51] Int. Cl.$^3$ .................. A61K 31/545; C07D 501/46
[52] U.S. Cl. ...................................... 424/246; 544/22; 544/25; 544/27; 544/28
[58] Field of Search .......................... 544/25; 424/246

[56] References Cited

U.S. PATENT DOCUMENTS 4,033,950  7/1977  Cook et al. .............................. 544/25
4,066,762  1/1978  Dunn et al. ............................. 544/27
4,098,888  7/1978  Ochiai ..................................... 544/25
4,202,893  5/1980  Heymes et al. ......................... 544/19

Primary Examiner—Paul M. Coughlan, Jr.
Attorney, Agent, or Firm—Wegner & Bretschneider

[57] ABSTRACT

A 7-[2-(2-aminothiazol-4-yl)-2-(syn)-methoxyiminoacetamido] cephalosporin derivative of the formula;

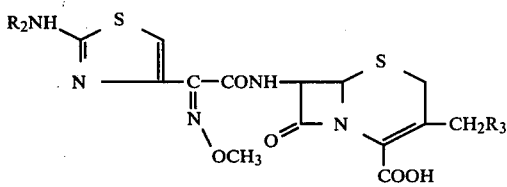

wherein $R_3$ is hydrogen or a residue of a nucleophilic compound; $R_2NH$ is an amino group which may optionally be protected, pharmaceutically acceptable salt or ester thereof, is found to have excellent anti-bacterial activity against a broad spectrum of bacteria inclusive of gram-negative bacteria such as *Escherichia coli, Serratia marcescens, Proteus rettgeri, Enterobacter cloacae* and *Citrobacter freundii*. Thus, this compound may be used for an antibacterial agent in therapeutical purposes.

4 Claims, No Drawings

7-[2-(2-AMINOTHIAZOL-4-YL)-2-(SYN)-METHOX-YIMINOACETAMIDO] CEPHALOSPORINS

This application is a continuation of application Ser. No. 787,258, filed Apr. 13, 1977, now abandoned.

This invention relates to novel cephalosporin derivatives having a novel 7-acyl group and processes for the production thereof. More particularly, this invention relates to 7-[2-(2-aminothiazol-4-yl)-2-(syn)-methoxyiminoacetamido]cephalosporin derivatives of the formula (I);

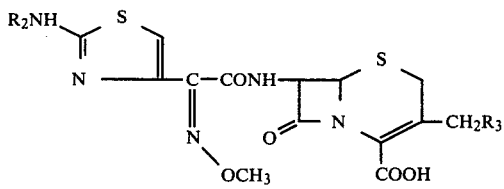

wherein $R_3$ is hydrogen or a residue of a nucleophilic compound; $R_2NH$ is an amino group which may optionally be protected, a pharmaceutically acceptable salt or ester thereof and also relates to processes for the production of the same.

Heretofore, studies on synthetic cephalosporin derivatives have been directed to the conversion of 7-aminocephalosporanic acid to various acyl derivatives at the 7-position or to derivatives at the 3-position in order to synthesize compounds having a broad anti-bacterial spectrum or a specific anti-bacterial spectrum. However, known cephalosporin derivatives are not satisfactory in anti-bacterial activity against a wide variety of microorganisms.

Under these circumstances, the present inventors et al. had found cephalosporin derivatives represented by the following formula;

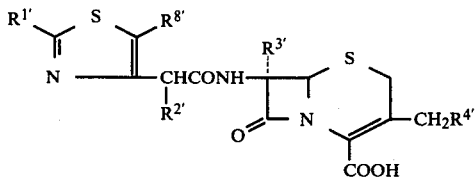

wherein $R^{1'}$ represents amino or hydroxyl group which may be protected, $R^{2'}$ represents amino or hydroxyl group or a group convertible into these groups, $R^{3'}$ represents hydrogen or methoxy group or a group convertible into methoxy group, $R^{4'}$ represents hydrogen or a residue of a nucleophilic compound and $R^{8'}$ represents hydrogen or a halogen, or a pharmaceutically acceptable salt or ester thereof (West German Patent Application Laid Open No. 2556736). Among these compounds the present inventors further found that the compounds of the formula (I) were highly active against a broad spectrum of gram-positive and gram-negative bacteria including *Serratia marcescens, Proteus morganii,* and further, that the compounds (I) were effective against β-lactamase producing bacteria. This invention have accomplished on the ground of these findings.

Referring to compound of the formula (I), $R_3$ is hydrogen or a residue of a nucleophilic compound. As examples of said residue of a nucleophilic compound which is represented by $R_3$ may be mentioned hydroxy; mercapto; acyloxy derived from lower aliphatic carboxylic acid having 2 to 4 carbon atoms, which may optionally be substituted by oxo, carboxy or ethoxycarbamoyl (e.g. acetyloxy, propionyloxy, 3-oxobutyryloxy, 3-carboxypropionyloxy, 3-ethoxycarbamoylpropionyloxy, 4-carboxybutyryloxy); acyloxy derived from aromatic carboxylic acid, which may optionally be substituted by hydroxy, carboxy, carboethoxycarbamoyl or carboethoxysulfamoyl, (e.g. mandelyloxy, 2-carboxybenzoyloxy, 2-(carboethoxycarbamoyl)benzoyloxy, 2-(carboethoxysulfamoyl)benzoyloxy); carbamoyloxy; cyano; azido; amino; carbamoylthio; thiocarbamoyloxy; carbamoyloxy whose amino group is protected by a conventional protecting group for amino function (e.g. N-mono-, -di- and trihalogenoacetylcarbamoyloxy groups such as N-chloroacetylcarbamoyloxy, N-dichloroacetylcarbamoyloxy, N-trichloroacetylcarbamoyloxy, N-chlorosulfonylcarbamoyloxy, N-trimethylsilylcarbamoyloxy, etc.); phenylglycyloxy; and so forth. These residues of a nucleophilic compound may be substituted, the number of substituents being normally from 1 to 2. Thus, the substituents on said residues which have been mentioned above may for example be alkyls (such as lower alkyls of 1 to 3 carbon atoms, e.g. methyl, ethyl, propyl, etc.) and acyl groups (such as acyls derived from lower aliphatic carboxylic acid having 2 to 4 carbon atoms, e.g. acetyl, propionyl, butyryl, etc.; acyls derived from aromatic carboxylic acid, e.g. benzoyl, p-chlorobenzoyl, p-methylbenzoyl, mandeloyl, etc.). The residue of a nucleophilic compound represented by $R_3$ may alternatively be a quaternary ammonium group. The residue represented by $R_3$ may further be a heterocyclic ring attached through S (sulphur atom), i.e. heterocyclic ring thio group represented by the formula -S-heterocyclic ring. The heterocyclic ring mentioned above is a five- or six-membered ring including 1 to 4 hetero-atoms selected from the group consisting of oxygen, sulphur and nitrogen atoms, and the nitrogen atom or atoms may be in oxide form. It follows, therefore, that said heterocyclic group (i.e. group derived from the heterocyclic compound corresponding to the heterocyclic ring) may usually be one of the following and other groups; pyridyl; N-oxidopyridyl; pyrimidyl; pyridazinyl, N-oxidopyridazinyl; pyrazolyl; diazolyl such as pyrazolyl, imidazolyl; thiazolyl such as 1,2-thiazolyl, 1,3-thiazolyl; thiadiazolyl such as 1,2,3-thiadiazolyl, 1,2,4-thiadiazolyl, 1,3,4-thiadiazolyl, 1,2,5-thiadiazolyl; oxadiazolyl such as 1,2,3-oxadiazolyl, 1,2,4-oxadiazolyl, 1,3,4-oxadiazolyl, 1,2,5-oxadiazolyl; triazolyl such as 1,2,3-triazolyl, 1,2,4-triazolyl; tetrazolyl such as 1H-tetrazolyl, 2H-tetrazolyl, etc. Such hetero group may each carry substituents such as lower alkyls of 1 to 3 carbon atoms (e.g. methyl, ethyl, i-propyl), allyl lower alkoxy groups of 1 to 3 carbon atoms (e.g. methoxy, ethoxy, propoxy), halogens (e.g. chlorine, bromine), trihalogenolower alkyls (e.g. trifluoromethyl, trichloroethyl), hydroxyl, mercapto, amino, carboxyl, carbamoyl, di-lower alkyl (having 1 to 3 carbon atoms) amino lower alkyl of 1 to 3 carbon atoms (e.g. dimethylaminoethyl, dimethylaminomethyl), carboxymethyl, carbamoylmethyl, carboxymethylthio, sulfomethyl, methoxycarbonylamino.

The number of such substituents that may occur on the heterocyclic group is normally in the range of 1 to 2. The quaternary ammonium group represented by $R_3$ may for example be pyridinium which may optionally be substituted by one member of methyl, halogen, carbamoyl, N-hydroxymethylcarbamoyl, carbomethoxycarbamoyl, cyanocarbamoyl, carboxymethyl, hydroxymethyl or trifluoromethyl such as pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl) pyridinium, 4-(N-cyanocarbamoyl)pyridinium, 4-(carboxymethyl)pyridinium, 4-(hydroxymethyl)pyridinium, 4-(trifluoromethyl)pyridinium; quinolinium; picolinium; lutidinium.

Referring to compounds of the formula (I), group represented by $R_3$ is preferably hydrogen, carbamoyloxy, acyloxy derived from lower aliphatic carboxylic acid having 2 to 4 carbon atoms such as acetyloxy, or the heterocyclic-thio group whose heterocyclic group is unsubstituted or substituted.

The preferred substituents of heterocyclic group of heterocyclic-thio group are one or two members of lower alkyl ($C_{1-4}$), di-lower alkyl ($C_{1-4}$) amino-substituted lower alkyl ($C_{1-4}$), carboxymethyl, amino, methoxycarbonylamino, carbamoylmethyl, carboxymethylthio or sulfomethyl. Among them, preferred $R^3$ is carbamoyloxy, 1-methyl-1H-tetrazol-5-ylthio, 2-methyl-1,3,4-thiadiazol-5-ylthio, 1,2-dimethyl-1,3,4-triazol-5-ylthio group and so on.

Where $R_3$ is a carbamoyloxy group whose amino group has been protected, e.g. N-chloroacetylcarbamoyloxy, N-dichloroacetylcarbamoyloxy or N-trichloroacetylcarbamoyloxy, such protecting group for the amino group may be removed by a procedure similar to that used for removing the protecting group from the protected amino group represented by $R_2NH—$, which is described hereinafter. Generally, the compound (I) is employed with its amino and carbamoyloxy group (where $R_1$ is carbamoyloxymethyl) being free and unprotected, as an active compound. Indicated by $R_2NH$ is an amino group which may optionally be protected. Therefore, $R_2$ means hydrogen or a protecting group for amino function, the latter being any of the per se known protective groups generally used for the protection of amino, i.e. conventional protecting group for amino function. Thus, such protective groups include, among others, aromatic acyl groups such as phthaloyl, benzoyl, benzoyl substituted by halogen, nitro or a lower alkyl of 1 to 4 carbon atoms (e.g. chlorobenzoyl, p-nitrobenzoyl, p-tert-butylbenzoyl, toluoyl), naphthoyl; phenylacetyl; phenoxyacetyl; benzenesulfonyl; benzenesulfonyl substituted by a lower alkyl of 1 to 4 carbon atoms (e.g. p-tertbutylbenzenesulfonyl, toluenesulfonyl); acyl derived from aliphatic or halogenated aliphatic carboxylic acid such as acetyl, valeryl, caprylyl, n-decanoyl, acryloyl, pivaloyl, halogenoacetyl (e.g. monochloroacetyl, monobromoacetyl, dichloroacetyl, trichloroacetyl); camphorsulfonyl; methanesulfonyl; esterified carboxyl groups such as ethoxycarbonyl, tert-butyloxycarbonyl, isobornyloxycarbonyl, phenyloxycarbonyl, trichloroethoxycarbonyl, benzyloxycarbonyl, etc.; carbamoyl groups such as methylcarbamoyl, phenylcarbamoyl, naphthylcarbamoyl, etc.; and the corresponding thiocarbamoyl groups.

The cephalosporin derivative of the formula (I) is thought to take a tautomeric form, i.e. a 2-aminothiazole compound and a 2-iminothiazoline compound as shown below, although it is described as the thiazole compound throughout this specification.

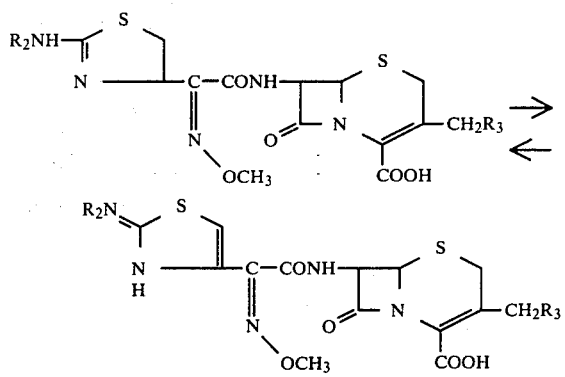

While the carboxyl group in 4-position of the compound of the formula (I) may be free, it may form a salt, for example with a nontoxic cation such as an alkali metal, e.g. sodium or potassium; a basic amino acid, e.g. arginine, ornithine, lysine or histidine; or a polyhydroxyalkylamine, e.g. N-methylglucamine, diethanolamine, triethanolamine or trishydroxymethylaminomethane. The compound (I) may form acid salt with an inorganic acid such as hydrogen chloride, sulfuric acid, etc. or with an organic acid such as toluenesulfonic acid, benzenesulfonic acid, etc. The 4-carboxyl group may also be one of those biologically active ester forms which conduce, for example, to increase of blood levels and prolonged efficacy. Such ester residues include lower alkoxymethyl groups, e.g. methoxymethyl, ethoxymethyl, isopropoxymethyl, α-methoxyethyl, α-ethoxyethyl, etc.; α-lower alkoxy-α-substituted methyl groups such as α-lower alkoxy($C_{1-4}$) ethyl (e.g. methoxyethyl, ethoxyethyl, propoxyethyl, i-propoxyethyl), etc.; lower alkylthiomethyl groups of 1 to 3 carbon atoms, e.g. methylthiomethyl, ethylthiomethyl, isopropylthiomethyl, etc.; acyloxymethyl groups, e.g. pivaloyloxy methyl, α-acetoxymethyl, etc.; ethoxycarbonyloxy-1-methylmethyl; or α-acyloxy-α-substituted methyl groups (e.g. α-acetoxy-α-methylmethyl). These salts and esters of compounds (I) also fall within the scope of the present invention.

As the known cephalosporins or penicillins, the compounds (I) according to this invention may be administered in such dosage forms as injections, capsules, tablets and granules. Thus, compounds (I) are novel compounds which show excellent activity against a broad spectrum of bacteria inclusive of gram-negative bacteria, such as *Escherichia coli, Serratia marcescens, Proteus rettgeri, Enterobacter cloacae* and *Citrobacter freundii,* and are resistant to β-lactamase. The compound (I) may be used, for example as a disinfectant for removing the aforesaid microorganisms from surgical instruments or as an antiinfective agent. Where the compound (I) is employed as an antiinfective agent, for example for the treatment of intraperitoneal infections, respiratory organ infections, urinary tract infections and other infectious diseases caused by the aforementioned microorganisms, it may be safely administered to mammals including humans, mice and rats at a daily dose level of 0.5 to 80 mg per kilogram body weight, preferably 1 to 20 mg on the same basis, in 3 to 4 installments daily. The compounds (I) may be administered orally or parenterally in varied dosage forms such as injections, capsules, powders, granules and tablets which may be manufactured by established or known arts. Where the compound (I) is used as an injection, the carrier may for example be distilled water or physiological saline. In the case the compound (I) is used as a capsule, powder, granule or tablet, the compound (I) is employed, for example in admixture with pharmacologically acceptable, per se known excipients (e.g. starch, lactose, sucrose, calcium carbonate, calcium phosphate), binders (starch, gum arabic, carboxymethyl-cellulose, hydroxypropylcellulose, crystalline cellulose, etc.), lubricants (e.g. magnesium stearate, talc, etc.), and disintegrating agents (e.g. carboxymethyl calcium, talc, etc.).

The compound (I) of this invention may be produced by a technique known per se.

(1) Thus, the cephalosporin derivative of the formula (I) is produced by acylating the 7-amino group of a 7-aminocephalosporin compound of the formula (II):

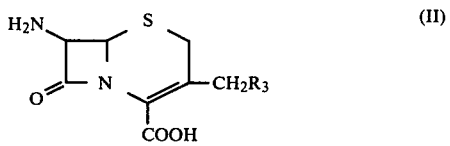

wherein $R_3$ is as previously defined with a 2-(2-aminothiazol-4-yl)-2-(syn)-methoxyimino acetic acid of formula (III):

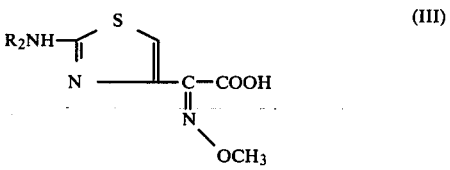

wherein $R_2NH$ is as previously defined, is necessary followed by removing the protective group for the amino group (Process I).

In this process, the compound (III) is employed, either as a free compound or in the form of a reactive derivative, as an acylating agent for the acylation of the amino group in 7-position on compound (II). Thus, the free acid (III), an alkali or alkaline earth metal salt of the free acid (III) (e.g. sodium, potassium or calcium salt), an organic amine salt of the free acid (III) (e.g. trimethylamine salt or pyridine salt), or a reactive derivative thereof [such as an acid halide (e.g. acid chloride or acid bromide), acid anhydride, mixed acid anhydride, active amide, active ester or the like] is subjected to the aforementioned acylation reaction. As examples of said active ester may be mentioned p-nitrophenyl ester, 2,4-dinitrophenyl ester, pentachlorophenyl ester, N-hydroxysuccinimide ester and N-hydroxyphthalimide ester. As examples of said mixed acid anhydride may be mentioned mixed acid anhydride with a carbonic acid monoester (e.g. carbonic acid monomethyl ester or carbonic acid monoisobutyl ester) and a mixed acid anhydride with a lower alkanoic acid which may be substituted by halogen (e.g. pivalic acid or trichloroacetic acid). Where the carboxylic acid (III) is employed as the free acid or in the form of a salt, there is employed a suitable condensing agent. As examples of said condensing agent may be mentioned N,N'-di-substituted carbodiimides, e.g. N,N'-dicyclohexylcarbodiimide; azolides, e.g. N,N'-carbonylimidazole and N,N'-thionyldiimidazole; dehydrating agents, e.g. N-ethoxycarbonyl-2-ethoxy-1,2-dihydroquinoline, phosphorus oxychloride and alkoxyacetylene; 2-halogenopyridinium salts (e.g. 2-chloropyridiniummethyl iodide, 2-fluoropyridiniummethyl iodide) and the like. Where such a condensing agent is employed, it is supposed that the reaction proceeds via the reactive derivative of the carboxylic acid (III). The reaction is generally conducted in a suitable inert solvent. As examples of such solvent may be mentioned halogenated hydrocarbons, e.g. chloroform, methylene dichloride, etc.; ethers, e.g. tetrahydrofuran, dioxane, etc.; dimethylformamide; dimethylacetamide; acetone; water and mixtures of such solvents. The proportion of said acylating agent is normally within the range of about 1 to 5, preferably 1 to 2, molar equivalents based on the compound (II). This reaction is generally carried out at a temperature in the range of $-50°$ to $+40°$ C. The reaction time is selected from the range of 1 to 10 hours, preferably 1 to 3 hours. Following the acylation reaction, the protective group for amino function may be removed, if necessary. The removal of the protective group for amino function may be generally accomplished by procedures known per se [e.g. by the procedure described in Japanese Patent Application Laid Open No. 52083/1975 and Pure and Applied Chemistry, 7, 335(1963)] or a procedure analogous thereto. It should be understood that where $R_2$ in the formula (I) is monohalogenoacetyl (e.g. monochloroacetyl) and $R_3$ is carbamoyloxy group whose amino group has been protected, such as N-monohalogenoacetylcarbamoyloxy (e.g. N-monochloroacetylcarbamoyloxy), these two monohalogenoacetyl groups (e.g. monochloroacetyl) may be simultaneously removed. In this sense, the protecting group for amino represented by $R_2$ is preferably a monohalogenoacetyl group. The reaction for removing the monohalogenoacetyl group from the amino group is performed by reacting a compound of formula (I) whose amino group or groups have been protected by monohalogeno acetyl with thiourea and a basic substance. Normally this reaction is conducted in a solvent at a temperature near room temperature and, in many instances, goes to completion in a time varying from 1 to 10 and odd hours. The solvent may be any solvent that will not interfere with the present reaction. Thus, there may be mentioned ethers, e.g. ethyl ether, tetrahydrofuran, dioxane, etc.; lower alcohols, e.g. methanol, ethanol, etc.; halogenated hydrocarbons, e.g. chloroform, methylene dichloride, etc.; esters, e.g. ethyl acetate, butyl acetate; ketones, e.g. acetone, methyl ethyl ketone, etc.; water; and various mixtures of such solvents.

This reaction for the removal of the N-halogenoacetyl group from the N-monohalogenoactylcarbamoyloxymethyl group in 3-position of the compound (I) does not proceed in any substantial extent when thiourea alone is permitted to act upon the compound (I). However, if the compound (I) is reacted with thiourea and a basic substance, the desired reaction for removing the monohalogenoacetyl group takes place selectively and smoothly to give the 3-carbamoyloxymethyl compound (I). As the basic substance used for the purposes of this reaction, there may be mentioned an alkali or alkaline earth metal salt of a lower aliphatic carboxylic acid or an inorganic or organic base having a pK value of not less than 9.5, preferably within the range of pKa 9.8 to 12.0. As examples of said salt of lower aliphatic carboxylic acid may be mentioned the salts of lower aliphatic carboxylic acids of 1 to 6 carbon atoms, such as sodium acetate, potassium acetate, calcium acetate, barium acetate, sodium formate, sodium propionate, potassium hexanoate, etc. As examples of said inorganic base may be mentioned the alkali metal salts of carbonic acid such as sodium carbonate, potassium carbonate, etc. The organic base may for example be one of the mono-, di- or tri-lower alkyl substituted amines whose lower alkyl is that of 1 to 4 carbon atoms, e.g. trimethylamine, triethylamine, ethylamine, methylamine, diethylamine, dimethylamine, tributylamine, dibutylamine, butylamine, etc.; and 5- to 6-membered cyclic amines substituted in N-position by lower alkyls of 1 to 2 carbon atoms such as N-methylpyrrolidine, N-ethylpyrrolidine, N-methylpiperazine, N-ethylpiperazine, etc. While, as aforesaid, thiourea is employed in this reaction, the reaction may also be successfully conducted with N- or N,N-substituted thiourea, such as methylthiourea, N,N-diethylthiourea or N,N-hexamethylenethiourea.

(2) The 7-[2-(2-aminothiazol-4-yl)-2-(syn)-methoxyiminoacetamido]cephalosporin derivative of the formula (V):

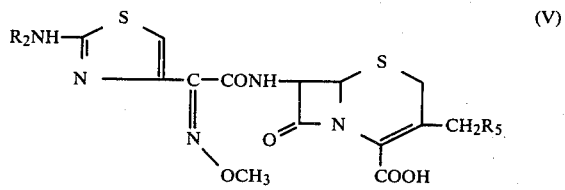

wherein $R_2NH$ is as previously defined; $R_5$ is a residue of a nucleophilic compound, is produced by reacting a compound of the formula (IV):

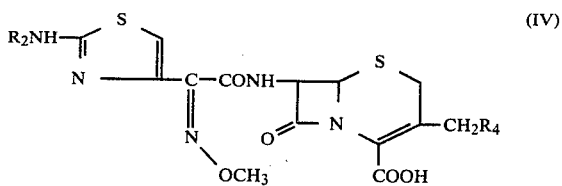

wherein $R_2NH$ is as previously defined; $R_4$ is acyloxy, carbamoyloxy or halogen, with a nucleophilic compound, if necessary followed by removal of the protective group for the amino group (Process 2).

As the acyloxy group represented by $R_4$ in the formula (IV), there may for instance be mentioned acyloxy derived from lower aliphatic carboxylic acid having 2 to 4 carbon atoms, which may optionally be substituted by oxo, carboxy or ethoxycarbamoyl, e.g. acetyloxy, propionyloxy, 3-oxobutyryloxy, 3-carboxypropionyloxy, 3-ethoxycarbamoylpropionyloxy, 4-carboxybutyryloxy, etc.; and acyloxy derived from aromatic carboxylic acid, which may optionally be substituted by hydroxy, carboxy, carboethoxycarbamoyl or carboethoxysulfamoyl, e.g. mandelyloxy, 2-carboxybenzoyloxy, 2-(carboethoxycarbamoyl)benzoyloxy and 2-(carboethoxysulfamoyl)benzoyloxy. The halogen represented by $R_4$ may for example be chlorine, bromine or iodine. The residue of a nucleophilic compound represented by $R_5$ in the formula (V) means the residue of a nucleophilic compound corresponding to the residue of a nucleophilic compound represented by $R_3$ excluding the acyloxy represented by $R_4$ or carbamoyloxy. For the purposes of this reaction, however, it is generally advantageous to employ a compound (IV) having an acyloxy group derived from lower aliphatic carboxylic acid such as acetyloxy. The nucleophilic compound employed in this reaction is a compound corresponding to the residue of a nucleophilic compound designated by the symbol $R_5$ in the formula (V). Particularly preferred are the heterocyclic thiol compounds i.e. mercapto compounds which may contain a substituent. Among the nucleophilic compounds corresponding to the residue represented by $R_5$, mercapto compounds may be employed in their free form, although it is advantageous to use them in the form of alkali metal salts, e.g. sodium or potassium salts. This reaction is preferably conducted in a solvent. For example, use is made of water, deuterium or an organic solvent that is readily miscible with water and does not react with the reactants, e.g. dimethylformamide, dimethylacetamide, dioxane, acetone, alcohol, acetonitrile, dimethylsulforxide and tetrahydrofuran. While the reaction temperature and time vary with such factors as the particular starting material and solvent employed, it is generally selected from the range of 0° to 100° C., preferably 30° to 70° C. and the range of 2 to 48 hours, preferably 3 to 15 hours, respectively. The reaction is preferably carried out in the neighborhood of neutrality and feasible within the range of about pH 2 to 8, preferably pH 5 to 8. The progress of this reaction may sometimes be rendered smooth by the addition of a quaternary ammonium salt having surface activity, such as trimethylbenzylammonium bromide or triethylbenzylammonium bromide or triethylbenzylammonium hydroxide. Moreover, more satisfactory results are obtained when the reaction is conducted in an inert gaseous atmosphere such as nitrogen in order to prevent atmospheric oxidation of the mercapto compound.

(3) The cephalosporin derivative of the formula (I) may also be produced by subjecting a 7-[2-(2-aminothiazol-4-yl)-2-(syn)-hydroxyiminoacetamido]cephalosporin derivative (VI):

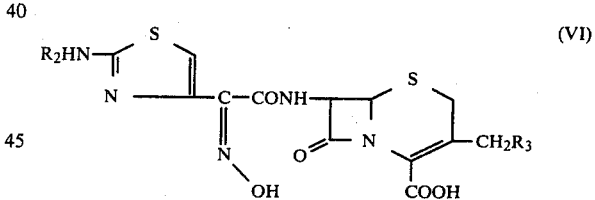

wherein R, and $R_2NH$ are as previously defined, to O-methylation. The O-methylation is conducted by reacting the compound (VI) with a methylating agent (Process 3).

This O-methylation reaction is normally conducted in a solvent under ice-cooling or in the neighborhood of room temperature (0° to 40° C., preferably 5° to 30° C.) and, in many cases, goes to completion with about 5 minutes to 5 hours, preferably 5 minutes to 2 hours. The solvent may be any solvent that will not interfere with the reaction, such as ethers, e.g. tetrahydrofuran, dioxane, etc.; lower alcohols, e.g. methanol, ethanol, etc.; halogenated hydrocarbons, e.g. chloroform, methylene chloride, etc.; esters, e.g. ethyl acetate, butyl acetate, etc.; amides, e.g. N,N-dimethylformamide, N,N-dimethylacetamide, etc.; water; and mixtures of such solvents. The methylating agent may be a methylating agent which is generally employed in organic chemistry, such as methyl halide (e.g. methyl iodide, methyl bromide), dimethyl sulfate, diazometane or the like.

This reaction may proceed smoothly in the presence of a suitable base except in the case of diazomethane. As such base, use is normally made of an inorganic base such as the alkali metal salts of carbonic acid (e.g. sodium carbonate, potassium carbonate), alkali metal hydroxides (e.g. sodium hydroxide, potassium hydroxide). Where the stability of compound (VI) is a consideration, however, sodium carbonate, potassium carbonate or the like is preferably employed. This reaction may also be conducted in a buffer at about pH 7.5 to 8.5.

The cephalosporin compounds (I) which are produced by the several production processes described hereinbefore may each be purified by procedures known per se, such as column chromatography, extraction, precipitation, recrystallization and so forth. If necessary, each of those compounds may be treated by per se known procedures to obtain the desired salts, esters, etc.

One of the starting materials for this invention, i.e. 2-(2-aminothiazol-4-yl)-2-(syn)-methoxyiminoacetic acid derivative (III) may be produced, for example by the several alternative processes described hereinafter in detail.

(I) In the first place, a 4-halogeno-3-oxo-2-oxyiminobutyric acid derivative of the formula (VII):

$$XCH_2COC-COOR_7 \quad (VII)$$
$$\underset{\underset{OR_6}{|}}{\overset{||}{N}}$$

wherein X is halogen, e.g. chlorine or bromine; $R_6$ is hydrogen or methyl; $R_7$ is a lower alkyl of 1 to 3 carbon atoms, e.g. methyl, ethyl or propyl is reacted with thiourea to obtain a 2-(2-aminothiazol-4-yl)-2-oxyiminoacetic acid derivative of the formula (VIII):

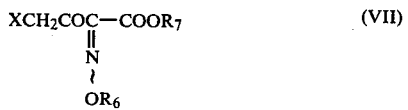

wherein $R_6$ and $R_7$ are as previously defined. In both the cases where $R_6$ is hydrogen and methyl, respectively, the compound (VIII) is normally obtained as a mixture of syn- and anti-isomers thereof. This reaction is normally conducted by reacting a compound of the formula (VII) with thiourea in an organic solvent such as ethanol, methanol or tetrahydrofuran at room temperature or elevated temperature (0° to 100° C., preferably 10° to 50° C.). The reaction time is selected from the range of 1 to 30 hours, preferably 1 to 5 hours. To isolate the desired syn-isomer from the resultant mixture of syn- and anti-forms of compound (VIII), one of the following procedures may be successfully followed. Thus, these procedures include the procedure of fractional crystallization which takes advantage of the differential crystallizabilities or solubilities of the isomers of the compound (VIII) as such, a salt of the compound (VIII) of hydrogen halide (HBr or HCl salt) or a derivative of the compound (VIII) with a protective group on its 2-amino group, the protective group (e.g. monochloroacetyl or dichloroacetyl) having been introduced by a procedure known per se; isolation by chromatography and a procedure such that when the compound (VIII) or the compound (VIII) with a protective group on its 2-amino group is hydrolyzed, at its ester position, by a per se known process to a carboxylic acid derivative of formula (III), the syn-isomer alone is selectively isolated by utilizing the difference in the rate of hydrolysis between the syn- and anti-isomers.

In the last-mentioned procedure, because of the higher rate of hydrolysis for the anti-isomer than for the syn-isomer, the anti-isomer may be selectively hydrolyzed and removed. The reaction for hydrolyzing the ester linkage of the compound (VIII) with or without a substituent on its 2-amino group is normally conducted in the presence of 1 to several molar equivalents of an alkali metal hydroxide, e.g. potassium hydroxide or sodium hydroxide at a temperature ranging from 0° C. to room temperature and in water or a mixture of water with an organic solvent miscible with water, e.g. methanol, ethanol, acetone, tetrahydrofuran, dioxane, N,N-dimethylformamide or N,N-dimethylacetamide. Where $R_6$ in the compound (VIII) is hydrogen, the syn-isomer isolated may be converted to syn-isomer of the compound (VIII) in which $R_6$ is methyl, by subjecting the former compound (VIII) to methylation. This methylation reaction is normally carried out in a solvent under ice-cooling or at temperatures near room temperature and, in many instances, goes to completion in a few minutes to several hours. The solvent for this purpose may be any type of solvent only if it does not interfere with the reaction. Thus, for example, tetrahydrofuran, dioxane, methanol, ethanol, chloroform, methylene dichloride, ethyl acetate, butyl acetate, N,N-dimethylformamide, N,N-dimethylacetamide and water as well as mixtures of such solvents may be mentioned. As the methylation agent may be mentioned methyl halides, e.g. methyl iodide and methyl bromide; dimethyl sulfate; and diazomethane; to name but a few. In all cases except that diazomethane is employed, the compound (VIII) in which $R_6$ is hydrogen is reacted with said methylating agent in the presence of a base such as an alkali metal carbonate (e.g. sodium carbonate, potassium carbonate, etc.) or an alkali metal hydroxide (e.g. sodium hydroxide, potassium hydroxide, etc.). Some of the physical constants of the syn-isomers of compounds (III) and (VIII) thus obtained are shown below in comparison with the physical constants of the corresponding anti-isomers (See Table 1).

TABLE 1

| Structure | NMR spectrum (ppm) | Melting point (°C.) |
|---|---|---|
| syn-isomer 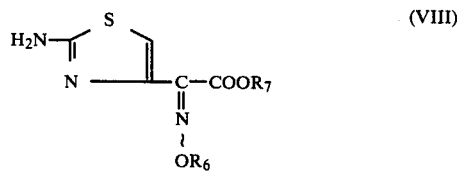 | In $d_6$-DMSO 6.80s(5-H) 11.6s(OH) | 185.5 |
| anti-isomer | In $d_6$-DMSO 7.50s(5-H) 12.5s(OH) | 145.3 |

TABLE 1-continued

| Structure | NMR spectrum (ppm) | Melting point (°C.) |
|---|---|---|
| syn-isomer: H$_2$N-thiazole-C(=N-OCH$_3$)-COOC$_2$H$_5$ | In CDCl$_3$ 6.74s(5-H) 4.02s (OCH$_3$) | 163 to 164 |
| anti-isomer: H$_2$N-thiazole-C(=N-OCH$_3$)-COOC$_2$H$_5$ (CH$_3$O on opposite side) | In CDCl$_3$ 7.43s(5-H) 4.07s (OCH$_3$) | 114 to 115 |
| syn-isomer: H$_2$N-thiazole-C(=N-OCH$_3$)-COOCH$_3$ | In CDCl$_3$ 6.74s(5-H), 4.02s (OCH$_3$) | 164.9 |
| anti-isomer: H$_2$N-thiazole-C(=N-OCH$_3$)-COOCH$_3$ | In CDCl$_3$ 7.48s(5-H), 4.06s (OCH$_3$) | — |
| syn-isomer: ClCH$_2$CONH-thiazole-C(=N-OCH$_3$)-COOC$_2$H$_5$ | In CDCl$_3$ 7.15s(5-H) 4.00s (OCH$_3$) | 111 to 112 |
| anti-isomer: ClCH$_2$CONH-thiazole-C(=N-OCH$_3$)-COOC$_2$H$_5$ | In CDCl$_3$ 7.94s(5-H) 4.10s (OCH$_3$) | 81 to 82 |
| syn-isomer: ClCH$_2$CONH-thiazole-C(=N-OCH$_3$)-COOH | In d$_6$-DMSO 7.57s(5-H) 3.95s (OCH$_3$) | 170 to 171 |
| anti-isomer: ClCH$_2$CONH-thiazole-C(=N-OCH$_3$)-COOH | In d$_6$-DMSO 8.00s(5-H) 4.00s (OCH$_3$) | 182 to 183 |
| syn-isomer: ClCH$_2$CONH-thiazole-C(=N-OCH$_3$)-COOCH$_3$ | In CDCl$_3$ 7.24s(5-H), 4.02s (OCH$_3$) | 130.8 |
| anti-isomer: ClCH$_2$CONH-thiazole-C(=N-OCH$_3$)-COOCH$_3$ | In CDCl$_3$ 8.02s(5-H) 4.12s (OCH$_3$) | — |

Remarks
s: singlet
The methoxyimino (hydroxyimino) group in "syn" isomer is cis to the carboxyl function, and in "anti" isomer trans to the carboxyl function.

(II) The procedure for selective production of compound (III) (syn-isomer) will hereinafter be described. Whereas the aforementioned reaction of the compound (VII) with thiourea yields a mixture of syn- and anti-isomers of compound (VIII), in many instances the anti-isomer of the compound (VIII) predominates. The inventor's study of the conditions of this cyclization reaction shed light on the conditions to conduce to a selective formation of the desired syn-isomer. Thus, if the reaction of the compound (VII) with thiourea to produce the compound (VIII) is conducted under the conditions described hereinbefore, the syn- and anti-isomers are normally produced in a ratio in the range of 2:98 to 50:50.

It has been found, however, that if this cyclization reaction is carried out in water or a mixture of water and a water-miscible solvent such as methanol, ethanol, acetone, tetrahydrofuran, dioxane, N,N-dimethylformamide, N,N-dimethylacetamide or N-methylpiperidone and in the presence of a basic substance, the syn-isomer of the compound (VIII) is selectively produced (normally in a ratio of about 85:15 to 100:0). As the basic substance useful for the purposes of this reaction, there may be mentioned alkali or alkaline earth metal salts of lower aliphatic carboxylic acids, and inorganic or organic bases having pKa values of not less than 9.5, preferably within the range of 9.8 to 12.0. As examples of said lower aliphatic carboxylic acid salts may be mentioned the salts of lower aliphatic carboxylic acids of 1 to 6 carbon atoms such as sodium acetate, potassium acetate, calcium acetate, barium acetate, sodium formate, sodium propionate, potassium hexanoate, etc.; while the inorganic bases mentioned above include alkali metal salts of carbonic acid such as sodium carbonate, potassium carbonate, etc. As said organic bases may be mentioned tri-lower alkylsubstituted amines whose lower alkyl is that of 1 to 4 carbon atoms such as trimethylamine, triethylamine, tributylamine, etc. and 5- to 6-membered cyclic amines substituted in N-position by lower alkyl of 1 to 2 carbon atoms such as N-methylpyrrolidine, N-ethylpyrrolidine, N-methylpiperazine, N-ethylpiperazine, etc. Where said N,N-dimethylformamide, N,N-dimethylacetamide or N-methylpyrrolidone is employed as the solvent, it is not always necessary to add the aforesaid basic substance. The reaction temperature and time are generally selected from the range of 0° to 50° C. (preferably 0° to 30° C.) and the range of 1 to 30 hours (preferably 1 to 5 hours), respectively.

(III) The compound (VIII) (syn-isomer) may also be selectively produced by the following procedure. Thus, in a further search for a method for selective production of the synisomer, we have discovered that by reacting a 2-aminothiazol-4-ylglyoxyl acid derivative of the formula (IX) with O-methylhydroxylamine, the syn-isomer of the methoximino compound may be selectively obtained.

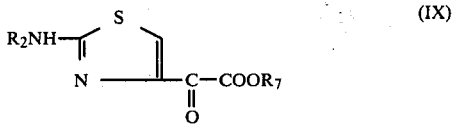

wherein $R_2$ and $R_7$ are as previously defined.

Normally this reaction may be conducted smoothy in a suitable solvent at pH about 4.0 to 9.0. The solvent mentioned may be any type of solvent unless it interferes with the reaction. Thus, for example, ethers such as ethyl ether, tetrahydrofuran, dioxane, etc.; lower alcohols such as methanol, ethanol, etc.; halogenated hydrocarbons such as chloroform, methylene dichloride, etc.; esters such as ethyl acetate, butyl acetate, etc.; water; and mixtures of such solvents may be mentioned. While this reaction proceeds in the neighborhood of room temperature, it may be accelerated by heating. The reaction temperature and time are generally selected from the range of 0° to 100° C. (preferably 0° to 50° C.) and the range of 1 to 10 hours (preferably 1 to 5 hours), respectively.

The starting compound (IX) for this reaction may be produced by the reaction described hereinafter. Thus, the hydrolysis of a nitron compound of the formula (X):

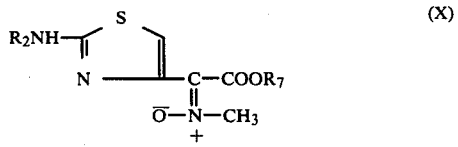

wherein $R_2$ and $R_7$ are as previously defined yields the compound (IX). This hydrolysis reaction takes place smoothly in the presence of a mineral acid, and is normally conducted in a solvent. As examples of said mineral acid may be mentioned hydrogen chloride, sulfuric acid, phosphoric acid, etc. The solvent may be of any desired type that will not interfere with the reaction. Thus, there may be mentioned ethers, e.g. tetrahydrofuran, dioxane, etc.; alcohols, e.g. methanol, ethanol, etc.; ketones, e.g. acetone, methyl ethyl ketone; water, and mixtures of such solvents. Normally this reaction may be conducted under ice-cooling or at room temperature.

The starting compound (X) may be obtained by subjecting a compound of the formula (VIII) wherein $R_6$ is hydrogen and whose amino group in 2-position has been protected, to methylation.

The conditions of this methylation reaction are essentially the same as the conditions under which the aforesaid compound (VIII) wherein $R_6$ is hydrogen is methylated. [cf. the aforesaid method (I)]

Under the described conditions of methylation, the methylation of the syn-isomer of the compound (VIII) wherein $R_6$ is hydrogen does not give any substantial amount of this nitron compound (X) but the methylation of the anti-isomer of the compound (VIII) wherein $R_6$ is hydrogen yields the nitron compound (X) as a dominant product.

The compound of the formula (VII) may be produced, for example by the methods described in Journal of Medicinal Chemistry, 16, 978(1973), Helvetica Chimica Acta, 49, 26(1966), Journal of the American Chemical Society, 60, 1328(1938) and West German Patent Application Laid Open (Offenlegungsschrift) No. 2556736, or by procedures similar to such methods. The compound of formula (II) used in this invention may be produced, for example by a suitable method selected from the methods described in U.S. Pat. Nos. 3875151 and 3697515, West German.patent application Laid Open No. 2461478, West German patent application Laid Open No. 2607064 (Dutch patent application No. 7601902), West German patent application Laid Open No. 2619243, Japanese Patent Application Laid Open No. 52083/1975, West German Patent Application Laid Open Nos. 2460331 and 2460332, or by a process analogous to such methods.

Among others, the compound (I) wherein $R_3$ is carbamoyloxy or monohaloacetylcarbamoyloxy group may also be produced, for example, by the method described below:

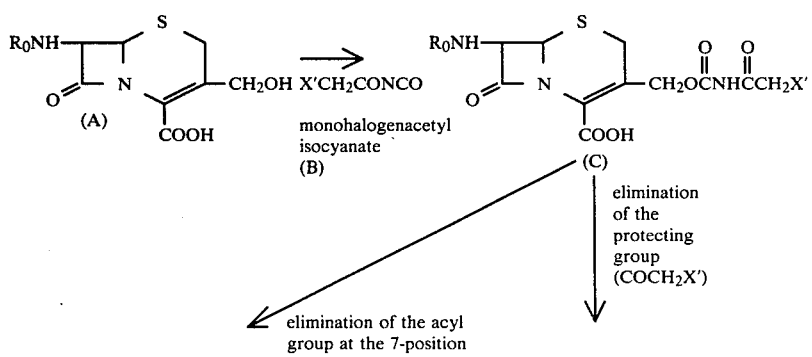

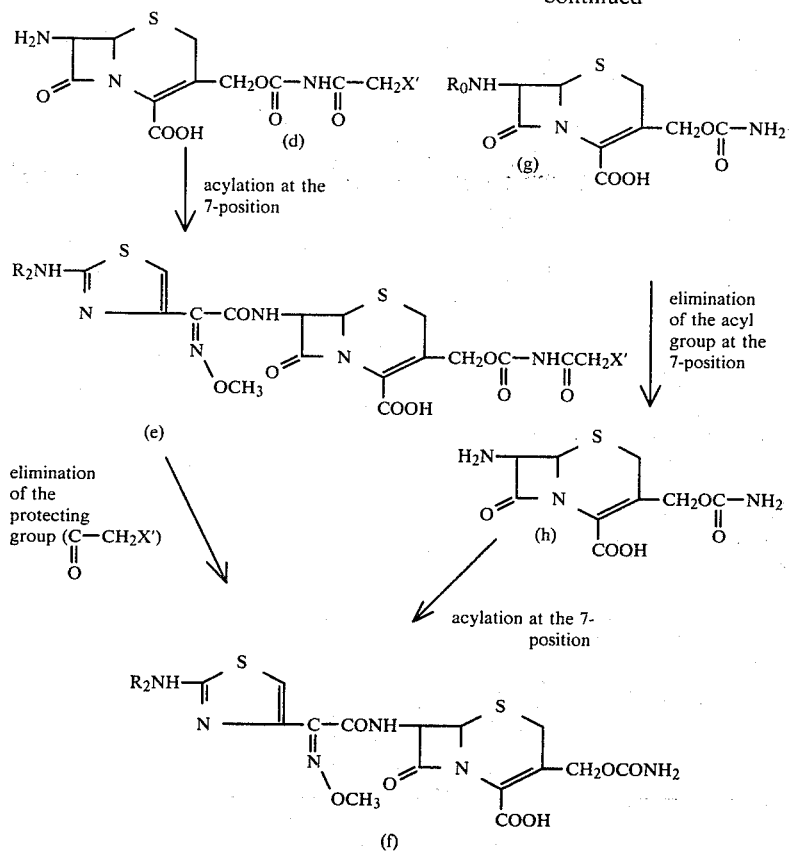

wherein $R_o$ is hydrogen or an acyl group, $X'$ is halogen such as chlorine, bromine or iodine and $R_2NH$ is as previously defined.

The reaction of the 3-desacetyl-cephalosporanic acid derivative of formula (A) with a monohalogenoacetyl isocyanate (B) is normally conducted smoothly by contacting the two reactants in a suitable solvent, either under ice-cooling or at a temperature near room temperature. The solvent employed for this purpose may be any solvent that will not interfere with this reaction. Thus, for examples, ethers such as ethyl ether, tetrahydrofuran, dioxane, etc.; ketones such as acetone, methyl ethyl ketone, etc.; halogenated hydrocarbons such as chloroform, methylene dichloride, trichloroethane, etc.; esters such as ethyl acetate, butyl acetate, etc.; and mixtures of such solvents may be mentioned. The amount of said monohalogenoacetyl isocyanate (B) is about 1 to several moles per mole of the starting compound (A). The monohalogenoacetyl isocyanate (B) may be produced, for example, by the method described in Journal of Organic Chemistry, 27, 3742 (1962) or a method analogous thereto.

The reaction for removing the 7-acyl group from the compound of formula (C) [or (g)] may be any of the reactions used generally for the deacylation of penicillins and cephalosporins. Thus, for example, the procedures described in West German Patent Application Laid Open Nos. 2460331 and 2460332, Japanese Patent Publication Nos. 13862/1966, 40899/1970 and No. 34387/1972 and U.S. Pat. No. 3632578, etc. may be successfully employed. By way of illustration, the compound (C) [or (g)] is treated with an imide halide-forming agent to obtain the corresponding imide halide in the first place and the latter compound is then treated with an alcohol to obtain the corresponding imide ether. This imide ether is hydrolyzed to the corresponding 7-amino derivative (d) [or (h)].

As said imide halide-forming agent, there may be employed one of the halides derived from carbon, phosphorus or/and sulfur and the acid halides derived from their oxy-acids (e.g. phosphorus oxychloride, phosphorus pentachloride, phosphorus trichloride, thionyl chloride, phosgene, oxalyl chloride, protocatechuoyl-phosphorus trichloride, p-toluenesulfonyl chloride, etc.), for instance. This imide-halide-forming reaction is normally conducted with advantage in a solvent. The solvents for this purpose include not only the common inert solvents (such as methylene dichloride, chloroform, etc.) but tertiary amines (e.g. triethylamine, pyridine, dimethylaniline, etc.) and other solvents as well as mixtures of such solvents. The imide ether-forming reaction is accomplished by contacting the imide halide reaction mixture with an alcohol. The alcohols that may be normally employed include lower alkanols containing 1 to 4 carbon atoms such as methanol, ethanol and n-butanol. The aforementioned hydrolysis is accomplished by contacting the reaction mixture containing the product imidoether with water. In order to preclude side reactions, the aforementioned reactions are preferably carried out under cooling.

The reaction for removing the monohaloacetyl group from the compound (c) [or (e)] is substantially the same reaction as that for removing the same group from the compound (I), which is described before.

Referring to the above formulas (A) and (B), the acyl groups represented by $R_o$ may be any of the following exemplary groups: via. acyl groups derived from straight-chain aliphatic carboxylic acid containing up to 10 carbon atoms and acyl groups derived from cycloaliphatic carboxylic acid of up to 6 carbon atoms, e.g. formyl, acetyl, propionoyl, hexanoyl, butanoyl, heptanoyl, octanoyl, cyclopentanoyl, etc.; acyl groups derived from phenyl- or phenoxy-substituted lower (up to 4 carbon atoms) aliphatic carboxylic acid, e.g. phenylacetyl, phenoxyacetyl, α-phenoxypropionyl, α-phenoxybutyryl, p-nitrophenylacetyl, etc.; acetyl or thioacetyl groups substituted by a 5- or 6-membered heterocyclic group including one N, S or O hetero-atom or a 5- or 6-membered heterocyclic group including said heteroatom and an additional 1 to 3 hetero-atoms selected from the class consisting of N, S and O, which latter heterocyclic group, in turn, may optionally be substituted by amino or hydroxyl, or by the corresponding heterocyclicoxy group, e.g. 2-thienylacetyl, tetrazolylacetyl, tetrazolylthioacetyl, α-(2-pyridyloxy)acetyl, α-(3-pyridyloxy)acetyl, α-(4-pyridyloxy)acetyl, 2-(2-hydroxy thiazol-4-yl)acetyl, 2-(2-aminothiazol-4-yl)acetyl, 4-pyridylthioacetyl, 1-pyrazolylacetyl, 2-furylacetyl, 6-(2'-oxo-3'-methylpyridazinyl)thioacetyl, etc.; acyl groups derived from mono-substituted aliphatic carboxylic acid, e.g. cyanoacetyl, acetoacetyl, ω-halogenoacetoacetyl, 4-methylthio-3-oxobutyryl, 4-carbamoylmethylthio-3-oxobutyryl, etc.; α-substituted phenylacetyl groups, e.g. mandelyl, α-carboxyphenylacetyl, α-aminophenylacetyl, α-sulfophenylacetyl, α-sulfo-(p-aminophenyl)acetyl, α-(β-methylsulfonylethoxycarbonyl)aminophenylacetyl, etc.; glycyl groups substituted in α-position by a 5- or 6-membered ring including one O or S atom as the hetero-atom or a 5- or 6-membered ring including said hetero-atom and one N atom as an additional hetero-atom, which latter ring is substituted by amino or hydroxyl, e.g. phenylglycyl, 1-cyclohexenylglycl, cyclohexadienylglycyl, thienylglycyl, p-hydroxyphenylglycyl, furylglycyl, 2-aminothiazol-4-ylglycyl, 2-hydroxythiazol-4-ylglycyl, etc.; acyl groups derived from di-substituted aliphatic carboxylic acid such as 5-amino-5-carboxyvaleryl, etc.; and heterocyclic acyl groups, e.g. 5-methyl-3-phenyl-4-isooxazolylcarbonyl, 3-(2,6-dichlorophenyl)-5-methyl-4-isooxazolylcarbonyl, etc.

The compound (A) may be produced generally ① by acylating 7-aminocephalosporanic acid (7-ACA) with an acylating agent corresponding to the acyl group represented by $R_o$ by per se known method for acylation of an amino group at 7-position of cephalosporin compound mentioned hereinbefore, and removing the 3-acetyl group enzymatically from the same cephalosporin having a 3-acetoxymethyl group [Biochemical Journal 81, 591(1961)] or ② by the fermentative production of 7-(D-5-aminoadipinamido)-3-hydroxymethyl-3-cephem-4-carboxylic acid (cephalosporadesic acid, desacetylcephalosporin C, DCPC) [Nature 246, 154(1973); Japanese Patent Laid Open No. 491/1974], for instance.

The optionally substituted heterocyclic thiol compound $R_5SH$, wherein $R_5$ is defined hereinbefore, which is employed as a nucleophilic compound in accordance with this invention may be synthesized, for example by the methods described in Journal für praktische Chemie, NF 133 (1932), Heterocyclic Compounds, 8, edited by Robert C. Elderfield (John Wiley & Sons) and Advances in Heterocyclic, Chemistry, edited by A. R. Katritaky, A. J. Boulton (Academic Press) or by processes analogous thereto.

The compound (IV) may be produced, for example, by the method described in Belgian patent No. 719710 or a process analogous thereto. As an alternative, it may be produced by the application of the aforementioned Process (1) to the compound (III) and the compound (II) wherein $—CH_2R_3$ is $—CH_2R_4$, which is obtainable by one of the methods mentioned hereinbefore as the methods for the production of the compound (II) or processes analogous thereto. The compound (VI) may be produced, for example, by a procedure analogous to the method described in West German Patent Application Laid Open No. 2556736, or by reacting the compound (II) with the syn-isomer of the compound (VIII) wherein $R_6$ is hydrogen.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g," "mg," "kg," "ml," "cm," "ppm," "Hz," "MHz," "mol," "m mol," "mcg," "Calcd.," "DMSO," "nm" and "decomp." are abbreviations of the "gram," "milligram," "kilogram," "milliliter," "centimeter," "part per million," "Herz," "mega Herz," "Mole," "milliMole," "microgram," "Calculated," "dimethylsulfoxide," "Nano meter," and "decomposed," respectively. Resins named "Amberlite" are products manufactured by Rohm & Haas Co. in U.S.A. All the temperatures are uncorrected and the percentages are all on the weight basis except specifically defined. The NMR spectra given therein were measured using a Varian Model HA 100 (100 MHz) or T60 (60 MHz) spectrometer with tetramethylsilane as the internal or external reference and all δ values are in ppm. Tye symbol s stands for a singlet, d a doublet, t a triplet, q a quartet, m a multiplet, and J a coupling constant.

REFERENCE EXAMPLE 1

In a solution of 13.3 g of sodium carbonate in 120 ml of water is dissolved 10 g of ethyl 3-oxo-2-hydroxyiminobutyrate, followed by addition of 30 ml of methanol. The mixture is cooled with ice and, under stirring, 15.8 g of dimethyl sulfate is added dropwise over a period of 3 minutes. After the dropwise addition has been completed, the ice-bath is removed and the mixture is stirred at room temperature for 40 minutes. The reaction mixture (pH 8 or higher) is extracted twice with ethyl acetate and the extracts are pooled, washed with water and dried. The solvent is then evaporated off under reduced pressure and the residue is subjected to distillation under reduced pressure. By the above procedure is obtained 9 g of ethyl 3-oxo-2-methoxyiminobutyrate as a pale-yellow oil boiling at 56°–61° C./0.3–0.4 mmHg.

Elemental analysis, for $C_7H_{11}NO_4$:
Calcd. C, 48.54; H, 6.40; N, 8.08,
Found C, 48.41; H, 6.51; N, 7.96.
NMR spectrum (60 MHz, in $CDCl_3$):
2.40 ppm(3H, singlet, $CH_3CO$), 4.10 ppm(3H, singlet, $=NOCH_3$)

REFERENCE EXAMPLE 2

(1) In 120 ml of chloroform is dissolved 27.3 g of ethyl 3-oxo-2-methoxyiminobutyrate and the solution is warmed to 40° C. Then, a solution of 25.3 g of bromine in 30 ml of chloroform is added dropwise over a period of 30 minutes. The mixture is stirred and reacted at room temperature for 1 hour. The reaction mixture is washed with a 5% aqueous solution of sodium hydrogen carbonate and water in that order and the organic layer is dried. The solvent is then distilled off under reduced pressure to obtain 36.2 g of ethyl 4-brom-3-oxo-2-methoxyiminobutyrate as an oily product.

NMR spectrum (60 MHz, in CDCl$_3$):
4.16 ppm(3H, singlet, OCH$_3$), 4.36 ppm(2H, singlet, BrCH$_2$CO)

(2) In 20 ml of ethanol is dissolved 5 g of the above product, followed by addition of 1.8 g of thiourea. The mixture is heated under reflux for 3 hours. After cooling, the precipitate is collected by filtration and dissolved in 20 ml of water, to which sodium hydrogen carbonate is added. The oil that has separated is extracted with ethyl acetate. The ethyl acetate layer is washed and dried. Thereafter, the ethyl acetate is evaporated off to obtain white crystals. Recrystallization from ethanol yields 2.6 g (57.2%) of ethyl 2-(2-aminothiazol-4-yl)-2-(anti)-methoxyiminoacetate as white crystals, melting point: 114°-115° C.

Elemental analysis, for C$_8$H$_{11}$N$_3$O$_3$S:
Calcd. C, 41.91; H, 4.84; N, 18.33,
Found C, 41.71; H, 4.75; N, 18.07.
NMR spectrum (60 MHz, in CDCl$_3$):
4.07 ppm(3H, s., OCH$_3$), 5.80 ppm(2H, br. s., NH$_2$), 7.43 ppm(1H, s., thiazole 5H)

(3) The filtrate obtained upon collection of the first crop of precipitate is concentrated under reduced pressure and sodium hydrogen carbonate is added to the residue. The mixture is extracted with ethyl acetate and the oil obtained from the ethyl acetate layer is purified by column chromatography on silica gel. By the above procedure is obtained 59 mg (1.3%) of ethyl 2-(2-aminothiazol-4-yl)-2-(syn)-methoxyiminoacetate as white crystals, melting point: 163°-164° C.

Elemental analysis, for C$_8$H$_{11}$N$_3$O$_3$S:
Calcd. C, 41.91; H, 4.84; N, 18.33,
Found C, 41.57; H, 4.76; N, 18.07.
NMR spectrum (60 MHz, in CDCl$_3$):
4.02 ppm(3H, s., OCH$_3$), 5.80 ppm(2H, br. s., NH$_2$), 6.74 ppm(1H, s., thiazole 5H)

REFERENCE EXAMPLE 3

To 600 ml of ethanol is added 121 g of ethyl 4-chloro-3-oxo-2-hydroxyiminoacetate together with 47.6 g of thiourea and the mixture is stirred at room temperature for 3 hours. The ethanol is then evaporated off under reduced pressure and 350 ml of water is added. The water layer is washed with ether, neutralized with sodium hydrogen carbonate (to pH 7.5) and extracted with ethyl acetate-tetrahydofuran (1:1). The organic layer is washed with water and dried. The solvent is then distilled off to obtain 45 g of crystalline product.

A 1 g portion of the above product is taken and purified by column chromatography on silica gel (eluting solvent: ethyl acetate-n-hexane). The first fraction gives 650 mg of the anti-isomer of ethyl 2-(2-aminothiazol-4-yl)-2-hydroxyiminoacetate and 150 mg of the syn-isomer is obtained from the second fraction. Anti-isomer: white crystals, melting point: 145.3° C. Syn-isomer: pale yellowish white crystals, melting point: 185.5° C.

Elemental analysis, for C$_7$H$_9$N$_3$O$_3$S:
Calcd. C, 39.06; H, 4.21; N, 19.51,
Found (Anti-) C, 38.81; H, 4.20; N, 19.62.
(Syn-) C, 39.28; H, 4.10; N, 19.63.
NMR spectrum (60 MHz, in d$_6$-DMSO):
Anti-isomer: 7.10 ppm(2H, br. s., NH$_2$), 7.50 ppm(1H, s., thiazole 5-H), 12.5 ppm(1H, s., OH).
Syn-isomer: 6.80 ppm(1H, s., thiazol-5-H), 7.12 ppm(2H, br. s., NH$_2$), 11.6 ppm(1H, s., OH)

REFERENCE EXAMPLE 4

In 150 ml of water is dissolved 10.6 g of sodium carbonate, followed by addition of a solution of 10.7 g of ethyl 2-(2-aminothiazol-4-yl)-2-(syn)-hydroxyiminoacetate in a mixture of 150 ml of tetrahydrofuran and 50 ml of methanol. Under ice-cooling, 12.6 g of dimethyl sulfate is added dropwise over a period of 5 minutes. After the dropwise addition has been completed, the ice-bath is removed and the mixture is stirred at room temperature. While stirring, white crystals start separating out. After 3 hours, most of the organic solvent is distilled off under reduced pressure and the residue is cooled with ice. The resultant precipitate is collected by filtration, washed with water and dried. By the above procedure is obtained 5 g of ethyl 2-(2-aminothiazol-4-yl)-2-(syn)-methoxyiminoacetate as white crystals. In NMR spectrum and other properties, this product is identified with the ethyl 2-(2-aminothiazol-4-yl)-2-(syn)-methoxyiminocetate.

REFERENCE EXAMPLE 5

In 10 ml of N,N-dimethylacetamide is dissolved 2.15 g of ethyl 2-(2-aminothiazol-4-yl)-2-(syn)-methoxyiminoacetate (melting point: 163°-164° C.) and, under ice-cooling, 1.27 g of chloroacetyl chloride is added dropwise. The mixture is stirred under ice-cooling for 30 minutes and, then, at room temperature for 30 minutes. The reaction mixture is diluted with 50 ml of water and extracted twice with 100 ml portions of ethyl acetate. The extracts are pooled, washed with a 5% aqueous solution of sodium hydrogen carbonate and a saturated aqueous solution of sodium chloride in the order mentioned and finally dried. The solvent is then evaporated off to obtain 2.04 g of ethyl 2-(2-chloroacetamidothiazol-4-yl)-2-(syn)-methoxyimioacetate as a crystalline product, melting point: 111°-112° C.

Elemental analysis, for C$_{10}$H$_{12}$N$_3$O$_4$SCl:
Calcd. C, 39.29; H, 3.96; N, 13.74,
Found C, 39.15; H, 3.91; N, 13.69.
NMR spectrum (60 MHz, in CDCl$_3$):
4.00 ppm(3H, s., =NOCH$_3$), 4.24 ppm(2H, s, ClCH$_2$CO),
7.15 ppm(1H, s., thiazol 5-H)

REFERENCE EXAMPLE 6

To a solution of 9 g of potassium hydroxide in a mixture of 85 ml of water and 452 ml of ethanol is added 9.62 g of ethyl 2-(2-chloroacetamidothiazol-4-yl)-2-(syn)-methoxyiminoacetate and the mixture is stirred at room temperature for 2 hours. The ethanol is distilled off under reduced pressure and, following addition of 85 ml of water, the residue is washed with 100 ml of ethyl acetate. The water layer is adjusted to pH 2 with 10% hydrochloric acid and extracted twice with 200 ml portions of ethyl acetate. The extracts are combined, washed with a saturated aqueous solution of sodium chloride and dried. The solvent is then distilled off to obtain 7.63 g of 2-(2-chloroacetamidothiazol-4-yl)-2-(syn)-methoxyiminoacetic acid as crystals melting at 170°-171° C.

Elemental analysis, for C$_8$H$_8$N$_3$O$_4$SCl:

Calcd. C, 34.60; H, 2.90; N, 15.13
Found C, 34,97; H, 3.03; N, 14.74
NMR spectrum (60 MHz, in $d_6$-DMSO):
3.95 ppm(3H, singlet, =NOCH$_3$), 4.40 ppm(2H, singlet, ClCH$_2$CO), 7.57 ppm(1H, singlet, thiazole 5-H)

REFERENCE EXAMPLE 7

2.38 g of a 7:8 mixture of the syn- and anti-isomers of ethyl 2-(2-aminothiazol-4-yl)-2-methoxyiminoacetate is chloroacetylated with chloroacetyl chloride as in Reference Example 5, and 30 ml of ether is added to the resultant mixture of the syn- and anti- forms of ethyl 2-(2-chloroacetamidothiazol-4-yl)-2-methoxyiminoacetate. The crystals that have separated out are collected by filtration [Product (A)]. In NMR spectrum and other properties, this product is identified with the sample of ethyl 2-(2-chloroacetamidothiazol-4-yl)-2-(syn)-methoxyiminoacetate obtained in Reference Example 5. Yield 600 mg.

The oil obtained upon concentration of the filtrate (2.42 g., a mixture of syn- and anti-isomers) is added to a solution of 879 mg potassium hydroxide in a mixture of 5 ml water and 80 ml ethanol under ice-cooling and the entire mixture is stirred at that temperature for 15 minutes. The ethanol is distilled off under reduced pressure and the residue is diluted with 50 ml of water and extracted twice with 100 ml portions of ethyl acetate. The ethyl acetate layer is washed with water and dried. The ethyl acetate is then distilled off to obtain 577 mg of ethyl 2-(2-chloroacetamidothiazol-4-yl)-2-(syn)-methoxyiminoacetate [Product (B)]. In NMR spectrum and other properties, this product is identified with the syn-isomer according to Reference Example 5. Products (A) and (B) give a total yield of 1076 g or a recovery rate of 96.8%.

REFERENCE EXAMPLE 8

In 600 ml of 50% aqueous tetrahydrofuran is dissolved 67.8 g of ethyl 4-chloro-3-oxo-2-hydroxyiminoacetate, followed by addition of 155 g of sodium acetate trihydrate and 53.2 g of thiourea. The mixture is stirred at room temperature for 4 hours. The reaction mixture is adjusted to pH 7.0 with sodium hydrogen carbonate and, following addition of sodium chloride, it is extracted twice with 300 ml of tetrahydrofuran. The extracts are combined, washed (with water) and dried. The tetrahydrofuran is then distilled off to obtain 27.5 g of ethyl 2-(2-aminothiazol-4-yl)-2-hydroxyiminoacetate as crystals. Based on NMR and other data, this product is found to be a 82:18 mixture of syn- and anti-isomers.

A similar reaction is carried out without using sodium acetate. Based on the same criteria, the resultant product is found to be a 25:75 mixture of syn- and anti-isomers.

REFERENCE EXAMPLE 9

The reaction of Reference Example 8 is repeated except that 50% aqueous ethanol is used in lieu of 50% aqueous tetrahydrofuran. In this case, too, where sodium acetate is employed, there is obtained an 83:17 mixture of syn- and anti-isomers of ethyl 2-(2-aminothiazol-4-yl)-2-hydroxyiminoacetate. In contrast, where sodium acetate is not employed, the above reaction yields a 50:50 mixture of syn- and anti-isomers. The proportions of syn and anti-isomers are determined by NMR spectra and other methods.

REFERENCE EXAMPLE 10

The reaction of Reference Example 9 is repeated except that N,N-dimethylacetamide is used in lieu of 50% aqueous tetrahydrofuran-sodium acetate. This procedure yields an 85:15 mixture of syn- and anti-isomers of ethyl 2-(2-aminothiazol-4-yl)-2-hydroxyiminoacetate.

REFERENCE EXAMPLE 11

In 10 ml of 50% aqueous ethanol is dissolved 200 mg of ethyl 2-aminothiazol-4-yl-glyoxylate, followed by the addition of 166 mg of O-methylhydroxylamine hydrochloride and, then, 168 mg of sodium hydrogen carbonate. The mixture is stirred in a closed vessel at 70° C. for 5 hours. The reaction mixture is concentrated under reduced pressure and the residue is diluted with 10 ml of water and extracted with ethyl acetate. The ethyl acetate layer is washed with water and dried. The ethyl acetate is then distilled off to obtain ethyl 2-(2-aminothiazol-4-yl)-2-methoxyiminoacetate as crystals. Based on NMR and other data, this product is found to be an 83:17 mixture of syn- and anti-isomers.

REFERENCE EXAMPLE 12

In 70 ml of ethanol containing 10% of HCl is suspended 2.44 g of the methylnitron of ethyl 2-(2-aminothiazol-4-yl)-2-(anti)-hydroxyiminoacetate, which is N-(2-aminothiazol-4-yl-ethoxycarbonyl)methylenemethylamine N-oxide, melting point: 184°–185° C. The mixture is stirred at room temperature for 16 hours. The reaction mixture is concentrated under reduced pressure and, following addition of 10 ml of water, the residue is adjusted to pH 7.5 with a 5% aqueous solution of sodium hydrogen carbonate and extracted with ethyl acetate. The ethyl acetate layer is washed with water and dried. The ethyl acetate is then distilled off and the residue is recrystallized from ethanol. By the above procedure is obtained 1.54 g of ethyl 2-aminothiazol-4-ylglyoxylate as yellow crystals melting at 143.3° C.

Elemental analysis, for $C_7H_8N_2O_3S$:
Calcd. C, 41.98; H, 4.02; N, 13.99,
Found C, 41.83; H, 4.14; N, 13.98.

REFERENCE EXAMPLE 13

In 50 ml of 1 N-hydrochloric acid is dissolved 1 g of the same N-(2-aminothiazol-4-yl-ethoxycarbonyl)methylenemethylamine N-oxide as used is Reference Example 12 and the solution is stirred at room temperature for 5 hours. The reaction mixture is neutralized with sodium carbonate and extracted with ethyl acetate. Thereafter, the procedure of Reference Example 12 is repeated to obtain 0.5 g of ethyl 2-aminothiazol-4-ylglyoxylate. Based on NMR and other data, this product is identified with the product obtained in Reference Example 12.

REFERENCE EXAMPLE 14

In 20 ml of ethanol containing 10% of HCl is suspended 1.2 g of the methylnitron of 2-(2-aminothiazol-4-yl)-2-(syn)-hydroxyiminoacetate, i.e. N-(2-aminothiazol-4-yl-ethoxycarbonyl)methylenemethylamine N-oxide, melting point: 111.6° C. and the suspension is stirred at room temperature for 16 hours. Thereafter, the procedure of Reference Example 12 is repeated to obtain 0.7 g of ethyl 2-aminothiazol-4-ylglyoxylate as yellow crystals. In NMR and other properties, this product is identical with the product according to Reference Example 12.

REFERENCE EXAMPLE 15

To a mixture of 10 ml tetrahydrofuran and 5 ml ethyl acetate is added 1 g of ethyl 2-(2-aminothiazol-4-yl)-2-(anti)-hydroxyiminoacetate (melting point: 145.3° C.), followed by addition of an excess of diazomethane-ether solution. The mixture is allowed to stand at room temperature for 2 days. After the residual diazomethane is decomposed with acetic acid, the reaction mixture is concentrated under reduced pressure and the residue is recrystallized from ethyl acetate. By the above procedure is obtained 0.8 g of the methylnitron compound, i.e. N-(2-aminothiazol-4-yl-ethoxycarbonyl)methylenemethylamine N-oxide as yellow crystals melting at 184°–185° C.

Elemental analysis, for $C_8H_{11}N_3O_3S$:
Calcd. C, 41.91; H, 4.84; N, 18.33,
Found C, 41.86; H, 4.75; N, 18.35.
NMR spectrum (60 MHz, in $CDCl_3$):
3.82 ppm(3H, singlet, $N^+$—$CH_3$), 5.27 ppm(2H, br. singlet, $NH_2$), 8.49 ppm(1H, singlet, thiazole 5-H)

REFERENCE EXAMPLE 16

To a solution of 23 mg sodium in 8 ml methanol is added 215 mg of ethyl 2-(2-aminothiazol-4-yl)-2-(anti)-hydroxyiminoacetate (melting point: 145.3° C.) and, at room temperature, 280 mg of methyl iodide is added. The mixture is stirred for 45 minutes, after which it is concentrated under reduced pressure. The residue is diluted with water (pH 7 or higher) and extracted with ethyl acetate. The ethyl acetate layer is washed with water, dried and concentrated. The residue is recrystallized from tetrahydrofuran-ethyl acetate. By the above procedure is obtained 160 mg of the methylnitron compound as yellow crystals. This product is completely identical with the product obtained in Reference Example 15.

REFERENCE EXAMPLE 17

The filtrate after collection of the precipitated ethyl 2-(2-aminothiazol-4-yl)-2-(syn)-methoxyiminoacetate from the concentrated reaction mixture in the procedure of Reference Example 4 is extracted with tetrahydrofuranethyl acetate (1:1) and the extract is washed with water, dried and concentrated. To the residual brown-colored oil is added 20 ml of tetrahydrofuran and the mixture is allowed to stand in a refrigerator overnight. The resultant crystals are collected by filtration and recrystallized from ethyl acetate. By the above procedure is obtained 1.3 g of the methylnitron of ethyl 2-(2-aminothiazol-4-yl)-2-(syn)-hydroxyiminoacetate, i.e. N-(2-aminothiazol-4-yl-ethoxycarbonyl)methylenemethylamine N-oxide as yellow crystals melting at 111.6° C.

Elemental analysis, for $C_8H_{11}N_3O_3S$:
Calcd. C, 41.91; H, 4.84; N, 18.33,
Found C, 41.89; H, 4.91; N, 18.44.
NMR spectrum (60 MHz, in $CDCl_3$):
4.14 ppm(3H, singlet, $N^+$—$CH_3$), 5.34 ppm(2H, br. singlet, $NH_2$), 6.62 ppm(1H, singlet, thiazole 5-H)

REFERENCE EXAMPLE 18

In 10 ml of tetrahydrofuran is dissolved 1.5 g of ethyl 4-brom-3-oxo-2-methoxyiminobutyrate and, after 7 ml of water is added, 2.4 g of sodium acetate trihydrate and 0.9 g of thiourea are further added. The mixture is stirred at room temperature for 17 hours, after which it is concentrated under reduced pressure. The concentrate is adjusted to pH about 1.5 with dilute hydrochloric acid and washed with ethyl acetate. The water layer is neutralized with sodium hydrogen carbonate and extracted with ethyl acetate. The ethyl acetate layer is washed with water, dried and concentrated under reduced pressure to obtain 0.8 g of yellowish crystals. This product is the ethyl 2-(2-aminothiazol-4-yl)-2-(syn)-methoxyiminoacetate. Based on NMR and other data, this product is identified with the syn-isomer obtained in Reference Example 2.

REFERENCE EXAMPLE 19

In 10 ml of dimethylformamide is dissolved 2 g of ethyl 4-brom-3-oxo-2-methoxyiminobutyrate, followed by addition of 1.2 g of thiourea. This mixture is reacted at room temperature for 5 hours. To the reaction mixture is added 20 ml of a saturated aqueous solution of sodium chloride and, then, the pH of the mixture is adjusted to pH about 1.5 with dilute hydrochloric acid. Thereafter, the procedure of Reference Example 18 is followed to obtain 1.1 g of pale-yellow crystals. Based on its NMR and other data, this product is identified to be an 87:13 mixture of the syn- and anti-isomers of ethyl 2-(2-aminothiazol-4-yl)-2-methoxyiminoacetate. Washing the product with a small quantity of ether gives the syn-isomer substantially free of the anti-isomer.

REFERENCE EXAMPLE 20

(1) In 80 ml of anhydrous acetone is dissolved 20 g of 7-(5-carboxy-5-benzamidovalerylamido)desacetylcephalosporanic acid, followed by addition of 7 g of chloroacetyl isocyanate. The mixture is stirred at 20° C. for 40 minutes, after which 200 ml of ether is added. The precipitate is collected by filtration and washed with 50 ml of ether. By the above procedure is obtained 19.6 g of 7-(5-carboxy-5-benzamidovalerylamido)-3-(N-chloroacetyl)carbamoyloxymethyl-3-cephem-4-carboxylic acid as white powder.

NMR spectrum (60 MHz, in $d_6$-DMSO):
3.54 ppm(2H, quartet, 2—$CH_2$), 4.50 ppm(2H, singlet, —$NHCOCH_2Cl$), 4.98 ppm

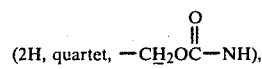
(2H, quartet, —$CH_2OC$—NH), 5.04 ppm(1H, doublet, 6-H), 5.77 ppm(1H, doublet, 7-H)

(2) In 80 ml of methylene dichloride containing 7.6 ml of N,N-dimethylaniline is suspended 6 g of 7-(5-carboxy-5-benzamidovalerylamido)-3-(N-chloroacetyl)-carbamoyloxymethyl-3-cephem-4-carboxylic acid. The mixture is cooled to −50° C., at which temperature 2.25 ml of phosphorus trichloride is added. It is then stirred at −30° C. for 1.5 hours to obtain a clear solution. To this solution is added 4.17 g of phosphorus pentachloride and the mixture is stirred at −25° C. for 2.5 hours, after which it is cooled to −40° C. and 37 ml of cold methanol is promptly added. The mixture is then stirred at −5° C. for 25 minutes and, following addition of 22 ml of water, it is adjusted to pH 3.5 with dilute aqueous ammonia. The reaction mixture is allowed to stand at 5° C. for 1 hour and the precipitate is collected by filtration. By the above procedure is obtained 1.76 g of 7-amino-3-(N-chloroacetyl)carbamoyloxymethyl-3-cephem-4-carboxylic acid as colorless crystals.

Elemental analysis, for $C_{11}H_{12}ClN_3O_6S$:
Calcd. C, 37.78; H, 3.46; N, 12.01,
Found C, 38.02; H, 3.86; N, 11.81.
NMR spectrum (60 MHz, in $CF_3COOH$):
3.78 ppm(2H, br. singlet, 2—$CH_2$), 4.35 ppm(2H, singlet, —NHCO$CH_2$Cl), 5.42 ppm(2H, br. singlet, 6-H, 7-H), 5.46 ppm(2H, quartet, —$CH_2$OCONH)

REFERENCE EXAMPLE 21

While a mixture of sodium azide, ethanol and water is stirred under reflux, an ethanolic solution of N,N-dimethylaminoethyl isothiocyanate is added dropwise. The mixture is further refluxed for 45 minutes, after which time the ethanol is distilled off under reduced pressure. The residual solution is made acidic with 1 N-hydrochloric acid and extracted with ethyl acetate. The extract is dried and concentrated to dryness and the crystalline residue is stirred with n-hexane, recovered by filtration and recrystallized from toluene. By the above procedure is obtained 1-(2-N,N-dimethylaminoethyl)-1H-tetrazol-5-thiol.

melting point: 217°–219° C. (recrystallized from aqueous ethanol)

NMR (60 MHz, in $D_2O+NaHCO_3$): δ3.03(s, N(CH$_3$)$_2$), 3.58 (t, $CH_2$), 4.70(t, $CH_2$)

REFERENCE EXAMPLE 22

(1) While a mixture of glycine-N,N-dimethylamide, triethylamine and methylene chloride is stirred, carbon disulfide and methyliodide are added in the order mentioned. The mixture is stirred at room temperature for 1 hour, after which it is shaken vigorously with a 5% aqueous solution of phosphoric acid. The organic layer is taken, washed with water, dried and concentrated to dryness under reduced pressure. The crystalline residue is stirred with n-hexane, recovered by filtration and dried. By the above procedure is obtained methyl 2-(N,N-dimethylcarbamoylmethyl)dithiocarbamate.

IR (KBr, cm$^{-1}$): 1626, 1543

NMR (60 MHz, in d$_6$-DMSO) δ: 2.62(s, CH$_3$S), 3.02(s, N(CH$_3$)$_2$), 4.42(d, J=4 Hz, CH$_2$), 8.30 (br. s., NH)

(2) A mixture of methyl 2-(N,N-dimethylcarbamoylmethyl)dithiocarbamate, sodium azide and ethanol is stirred under heating at 80° C. for 6.5 hours. The reaction mixture is adjusted to pH 2.5 with 10% hydrochloric acid and, then, concentrated to dryness under reduced pressure. The residue is extracted with 100 ml of methanol and the methanol extract is treated with activated carbon and dried. The residual powder is recrystallized from water By the above proedure is obtained 1-N,N-dimethylcarbamoylmethyl-1H-tetrazol-5-thiol.
melting point: 195°–198° C. (decomp.)

NMR (60 MHz, in d$_6$-DMSO) δ: 2.87 & 3.07 (each s, N(CH$_3$)$_2$), 5.21 (s, CH$_2$CO)

(3) Using a solution of sodium hydroxide, 1-N,N-dimethylcarbamoylmethyl-1H-tetrazole-5-thiol is hydrolyzed to obtain 1-carboxymethyl-1H-tetrazole-5-thiol.

melting point: 156°–160° C. (decomp.)
IR (KBr, cm$^{-1}$): 1713
NMR (60 MHz, in d$_6$-DMSO) δ: 5.03 (s, CH$_2$CO), 12.09 (br. s, NH & —COOH)

REFERENCE EXAMPLE 23

To 200 ml of water are added 38 g of sodium nitrite and 53 g of methyl acetoacetate and, under ice-cooling and stirring, 200 ml of 4N-sulfuric acid is added dropwise over a period of about an hour. During this dropwise addition, the temperature of the reaction mixture is maintained at 5°–8° C. The mixture is further stirred within that temperature range for 2.5 hours, after which it is extracted twice with 300 ml portions of ethyl acetate. The extracts are pooled and washed twice with a saturated aqueous solution of sodium chloride. Then, a solution of 96.7 g sodium carbonate in 1 l of water is divided into 3 equal portions, with which 3-oxo-2-hydroxyiminobutyrate is extracted from the above ethyl acetate layer (3 times). To the water layer (1 l) is added 200 ml of methanol and, after cooling with ice, 150 g of dimethyl sulfide is added dropwise with stirring over a period of 10 minutes. After the dropwise addition has been completed, the mixture is stirred at room temperature for 1.5 hours and extracted twice with 300 ml portions of ethyl acetate. The extracts are pooled, washed with water and dried. The ethyl acetate is then distilled off and the residue is cooled with ice, whereupon it solidifies. The solid residue is collected by filtration and washed with a small amount of water. By the above procedure is obtained 52.3 g of methyl 3-oxo-2-methoxyiminobutyrate as white crystals melting at 64.4° C.

Elemental analysis, for $C_6H_9NO_4$:
Calcd. C, 45.28; H, 5.70; N, 8.80
Found C, 44.93; H, 5.61; N, 8.71
NMR spectrum (60 MHz, in CDCl$_3$): 2.40 ppm(3H, singlet,

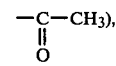

3.86 ppm(3H, singlet, COOCH$_3$), 4.10 ppm(3H, singlet, =NOCH$_3$)

REFERENCE EXAMPLE 24

In 150 ml of chloroform is dissolved 40 g of methyl 3-oxo-2-methyliminobutyrate and the solution is heated to 40° C. Then, a solution of 40 g bromine in 50 ml chloroform is added dropwise over a period of an hour. Thereafter, the reaction is continued under stirring at room temperature for an hour. The reaction mixture is washed with a 5% aqueous solution of sodium hydrogen carbonate and water in the order mentioned, and the organic layer is dried. The solvent is then distilled off to obtain 52.1 g of methyl 4-bromo-3-oxo-2-methoxyiminobutyrate as an oil.

NMR spectrum (60 MHz, in CDCl$_3$): 3.82 ppm(3H, singlet, COOCH$_3$), 4.09 ppm(3H, singlet, =N—OCH$_3$), 4.27 ppm(2H, singlet, BrCH$_2$CO)

In 350 ml of tetrahydrofuran is dissolved 52 g of methyl 4-bromo-3-oxo-2-methoxyiminobutyrate, followed by addition of 250 ml of water and, further, by the addition of 89.1 g of sodium acetate trihydrate and 33.2 g of thiourea. The mixture is stirred at room temperature for 18 hours. To the reaction mixture is added 200 ml of a 5% aqueous solution of sodium hydrogen carbonate, followed by extraction with ethyl acetate. The organic layer is washed with water, dried and concentrated under reduced pressure to remove the solvent. To the concentrate is added 200 ml of ether and the resultant precipitate is collected by filtration. By the above procedure is obtained 24.8 g of methyl 2-(2-aminothiazol-4-yl)-2-(syn)-methoxyiminoacetate as crystals melting at 164.9° C.

Elemental analysis, for $C_7H_9N_3O_3S$:

Calcd. C, 39.06; H, 4.21; N, 19.52,
Found C, 38.78; H, 4.15; N, 19.33.

NMR spectrum (60 MHz, in CDCl$_3$): 3.84 ppm(3H, singlet, COOCH$_3$), 4.02 ppm(3H, singlet, =NOCH$_3$), 5.74 ppm(2H, br. singlet, NH$_2$), 6.74 ppm(1H, singlet, thiazole 5-H)

REFERENCE EXAMPLE 25

In 90 ml of N,N-dimethylacetamide is dissolved 21.5 g of methyl 2-(2-aminothiazol-4-yl)-2-(syn)-methoxyiminoacetate and, under ice-cooling, 13.6 g of chloroacetyl chloride is added dropwise. The mixture is stirred under ice-cooling for 30 minutes and, then, at room temperature for 30 minutes. Following the addition of 500 ml of water, the reaction mixture is extracted twice with ethyl acetate. The extracts are pooled, washed with a 5% aqueous solution of sodium hydrogen carbonate and water in that order and dried. The solvent is then distilled off to obtain 25 g of methyl 2-(2-chloroacetamidothiazol-4-yl)-2-(syn)-methoxyiminoacetate as crystals melting at 130.8° C.

Elemental analysis, for C$_9$H$_{11}$N$_3$O$_4$SCl
Calcd. C, 37.03; H, 3.45; N, 14.40,
Found C, 37.30; H, 3.40; N, 14.35.

NMR spectrum (60 MHz, in CDCl$_3$): 3.90 ppm(3H, singlet, COOCH$_3$), 4.02 ppm(3H, singlet, =NOCH$_3$), 4.26 ppm(2H, singlet, ClCH$_2$CO), 7.24 ppm(1H, singlet, thiazole 5-H)

REFERENCE EXAMPLE 26

To a solution of 19.2 g of potassium hydroxide in a mixture of 170 ml water and 900 ml ethanol is added 20 g of methyl 2-(2-chloroacetamidothiazol-4-yl)-2-(syn)-methoxyiminoacetate and the solution is stirred at room temperature for 2 hours. The ethanol is distilled off under reduced pressure and, following the addition of 170 ml of water, the residue is washed with 200 ml of ethyl acetate. The water layer is adjusted to pH 2 with 10% hydrochloric acid and extracted twice with 300 ml portions of ethyl acetate.

The extracts are pooled, washed with a saturated aqueous solution of sodium chloride and dried. The solvent is distilled off to obtain 16.8 g of 2-(2-chloroacetamidothiazol-4-yl)-2-(syn)-methoxyiminoacetic acid as crystals. In NMR spectrum and other properties, this product is found to be identical with the product obtained in Reference Example 6.

REFERENCE EXAMPLE 27

(1) Six grams of the 7-(5-carboxy-5-benzamidovalerylamido)-3-(N-chloroacetyl)carbamoyloxymethyl-3-cephem-4-carboxylic acid is suspended in 80 ml of methylene dichloride containing 7.6 ml of N,N-dimethylaniline and, under cooling at −50° C., 2.25 ml of phosphorus trichloride is added. The mixture is stirred at −30° C. for 1.5 hours until a clear solution is obtained. To this solution is added 4.17 g of phosphorus pentachloride and the mixture is stirred at −25° C. for 2.5 hours. Then, it is cooled to −40° C. and 37 ml of cold methanol is promptly added. The mixture is stirred at −5° C. for 25 minutes, after which it is diluted with 22 ml of water and adjusted to pH 3.5 with dilute aqueous ammonia. The reaction mixture is allowed to stand at 5° C. for 1 hour and the resultant precipitate is collected by filtration. By the above procedure is obtained 1.76 g of 7-amino-3-(N-chloroacetyl)-carbamoyloxymethyl-3-cephem-4-carboxylic acid as a colorless crystalline product.

Elemental analysis, for C$_{11}$H$_{12}$ClN$_3$O$_6$S:
Calcd. C, 37.78; H, 3.46; N, 12.01,
Found C, 38.02; H, 3.86; N, 11.81.

NMR spectrum (60 MHz, in CF$_3$COOH): 3.78 ppm(2H, broad singlet, 2—CH$_2$), 4.35 ppm(2H, singlet, —NHCOCH$_2$Cl), 5.42 ppm(2H, broad singlet, 6-H, 7-H), 5.46 ppm(2H, quartet, —CH$_2$OCONH)

(2) In N,N-dimethylacetamide is dissolved 1.05 g of the 7-amino-3-(N-chloroacetyl)carbamoyloxymethyl-3-cephem-4-carboxylic acid obtained in the above (1) and, under ice-cooling, 998 mg of 2-chloroacetamidothiazol-4-yl-α-(anti)-methoxyiminoacetyl chloride hydrochloride is added. The mixture is stirred under ice-cooling for 15 minutes and, then, at room temperature for 2 hours. Then, following addition of 50 ml of water, the reaction mixture is extracted twice with 100 ml portions of ethyl acetate. The organic layers are pooled, washed with a saturated aqueous solution of sodium chloride and dried over magnesium sulfate. The ethyl acetate is then distilled off. By the above procedure is obtained 2.2 g of 7-[(2-chloroacetamidothiazol-4-yl)-α-(anti)-methoxyimino]-acetamido-3-(N-chloroacetyl)carbamoyloxymethyl-3-cephem-4-carboxylic acid as white powder.

Note: Production of 2-chloroacetamidothiazol-4-yl-α-(anti)-methoxyiminoacetyl chloride (i) In 100 ml of dimethylacetamide is dissolved 10 g of ethyl α-(anti)-methoxyimino-α-(2-aminothiazol-4-yl)-acetate and, under cooling with ice, 5.91 g of chloroacetyl chloride is added dropwise. The mixture is stirred at room temperature for 1 hour, at the end of which time it is poured in ice-water. The mixture is extracted with ethyl acetate and the organic layer is washed, dried and distilled to remove the solvent. By the procedure is obtained 12.66 g of ethyl α-(anti)-methoxyimino-α-[2-(chloroacetamido)thiazol-4-yl]acetate as crystals, melting point: 81°–82° C.

Elemental analysis, for C$_{10}$H$_{12}$N$_3$O$_4$SCl:
Calcd. C, 39.29; H, 3.96,
Found C, 38.74; H, 3.58.

The nuclear magnetic resonance spectrum (60 MHz, in CDCl$_3$) of this product gives singlets, one at 4.10 ppm being assignable to methoxy protons, at 4.24 ppm assignable to chloroacetyl protons and at 7.94 ppm assignable to thiazole 5-hydrogen.

(ii) 12.66 g of ethyl α-(anti)-methoxyimino-α-[2-(chloroacetamido)thiazol-4-yl]acetate is added to a solution of 11.74 g of potassium hydroxide in a mixture of 25 ml water and 500 ml ethanol. The mixture is stirred at room temperature for 20 minutes and ethanol is distilled off under reduced pressure and the residue is diluted with water. The mixture is acidified to 1 N-hydrochloric acid and the resultant precipitate is collected by filtration. By the above procedure is obtained 10.54 g of α-(anti)-methoxyimino-α-[2-(chloroacetamido)thiazol-4-yl]acetic acid, melting point: 182°–183° C.

Elemental analysis, for C$_8$H$_8$N$_3$O$_4$SCl:
Calcd. C, 34.60; H, 2.90; N, 15.13,
Found C, 34.53; H, 3.00; N, 14.80.

The nuclear magnetic resonance spectrum (60 MHz, in d$_6$-DMSO) of the above product shows singlets, assignable to methoxy protons at 400 ppm, chloroacetyl protons at 4.38 ppm and thiazole 5-hydrogen at 8.00 ppm, respectively. (iii) In 5 ml of methylene chloride is suspended 555.4 mg of α-(anti)-methoxyimino-α-[2-(chloroacetamido)thiazol-4-yl]acetic acid and, under ice-cooling, 416.3 mg of phosphorus pentachloride is added. The mixture is reacted under stirring for 30 minutes. To the reaction mixture is added n-hexane and the resultant precipitate is collected by filtration. By the above procedure is obtained 620 mg of α-(anti)-methoxyimino-α-[2-(chloroacetamido)thiazol-4-yl]acetyl chloride hydrochloride.

Elemental analysis, for $C_8H_7N_3O_3SCl_2 \cdot HCl$:
C, 28.89; H, 2.42; N, 12.63,
C, 28.35; H, 2.81; N, 12.00.

(3) In 50 ml of tetrahydrofuran is dissolved 2.2 g of the 7-[2-chloroacetamidothiazol-4-yl)-α-(anti)-methoxyimino]acetamido-3-(N-chloroacetyl)carbamoyloxymethyl-3-cephem-4-carboxylic acid obtained in the above (2), followed by the addition of 913 mg of finely powdered thiourea and 1.63 g of sodium acetate trihydrate. The mixture is stirred at room temperature for 17 hours. The precipitate is collected by filtration, washed with ethyl ether and dissolved in 10 ml of water. The solution is made to pH 7 with sodium hydrogen carbonate and passed through a column of Amberlite XAD-2. By the above procedure is obtained 360 mg of sodium 7-[(2-aminothiazol-4-yl)-α-(anti)-methoxyimino)acetamido-3-carbamoyloxymethyl-3-cephem-4-carboxylate as white powder, Elemental analysis, for $C_{15}H_{15}N_6O_7S_2Na \cdot 2.5H_2O$:
Calcd. C, 34.42; H, 3.85; N, 16.05,
Found C, 34.43; H, 3.70; N, 15.68.

NMR spectrum (60 MHz, in $D_2O$):
3.55 ppm(2H, quartet, 2—$CH_2$), 4.11 ppm(3H, singlet, =NOCH$_3$), 4.81 ppm(2H, quartet, —C$\underline{H}$$_2$OCONH$_2$), 5.21 ppm(1H, doublet, 6-H), 5.82 ppm(1H, doublet, 7-H), 7.55 ppm

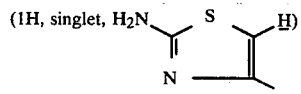

(1H, singlet, H$_2$N—S—$\underline{H}$)

The antibacterial activity [MIC (γ/ml)] of the sodium 7-[(2-aminothiazol-4-yl)-α-(anti)-methoxyimino]acetamido-3-carbamoyloxymethyl-3-cephem-4-carboxylate according to this example is shown below.

| Microorganism | | MIC(γ/ml) |
|---|---|---|
| Escherichia coli | 0-111 | 0.78 |
| Klebsiella pneumoniae | DT | 1.56 |
| Klebsiella pneumoniae | GN 3835 | 6.25 |
| Serratia marcescens | IFO 12648 | 12.5 |
| Serratia | TN0024 | 6.25 |
| Proteus vulgaris | IFO 3988 | 0.39 |
| Proteus mirabilis | GN 4359 | 0.78 |
| Proteus morganii | IFO 3168 | 0.78 |
| Proteus rettgeri 8 | TNO 336 | <0.2 |
| Proteus rettgeri | GN 4733 | 0.78 |
| Enterobacter cloacae | IFO 12937 | 25 |
| Citrobacter freundii | GN 99 | 1.56 |
| Citrobacter freundii | GN 1706 | 3.13 |

REFERENCE EXAMPLE 28

(1) In 20 ml of N,N-dimethylacetamide is dissolved 1.05 g of 7-amino-3-(N-chloroacetyl)carbamoyloxymethyl-3-cephem-4-carboxylic acid and, under ice-cooling, 869 mg of 2-chloroacetamidothiazol-4-ylacetyl chloride hydrochloride is added. The mixture is stirred under ice-cooling for 15 minutes and, then, at room temperature for 2 hours. After this reaction, the mixture is diluted with 50 ml of water and extracted twice with 100 ml portions of ethyl acetate. The organic layers are pooled, washed with a saturated aqueous solution of sodium chloride and dried over magnesium sulfate. The ethyl acetate is then distilled off to obtain white powder of 7-(2-chloroacetamidothiazol-4-yl)acetamido-3-(N-chloroacetyl)carbamoyloxymethyl-3-cephem-4-carboxylic acid.

Yield 1.6 g.

Note: Production of 2-chloroacetamidothiazol-4-ylacetyl chloride

In 15 ml of dimethylacetamide is dissolved 4 g of ethyl 2-aminothiazol-4-ylacetate and, under ice-cooling, 3.62 g of chloroacetyl chloride is added dropwise. The mixture is stirred under ice-cooling for 30 minutes and, then, at room temperature for another 30 minutes. Then, following the addition of 50 ml of water, the mixture is extracted twice with 100 ml portions of ethyl acetatetetrahydrofuran. The extract is washed with 100 ml of a 5% aqueous solution of sodium hydrogen carbonate and, then, with 100 ml of a saturated aqueous solution of sodium chloride, followed by drying. The solvent is then distilled off. By the above procedure is obtained 2.95 g of ethyl 2-chloroacetamidothiazol-4-ylacetate as an oily product. The entire amount of this oil is suspended in 100 ml of methanol and, under ice-cooling, 12 ml of water containing 761 mg of sodium hydroxide is added. The mixture is stirred at room temperature for 30 minutes, at the end of which time a major portion of the methanol as distilled off under reduced pressure. To the residue is added 10 ml of water. The water layer is washed with 50 ml of ethyl acetate and after the addition of 20 ml of ethyl acetate, it is adjusted to pH 2 with 10% hydrochloric acid. The mixture is shaken well and the organic layer is taken, washed with a saturated aqueous solution of sodium chloride and dried. The solvent is then distilled off. By the above procedure is obtained 1.51 g of 2-chloroacetamidothiazol-4-ylacetic acid as colorless crystals, melting point: 202°–203° C.

Elemental analysis, for $C_7H_7ClN_2O_3S$:
Calcd. C, 35.83; H, 3.01; N, 11.94,
Found C, 36.01; H, 2.96; N, 11.61.

In 20 ml of methylene dichloride is suspended 938 mg of the above product and, under ice-cooling, 1 g of phosphorous pentachloride is added. The mixture is stirred at room temperature for 30 minutes. Following addition of 50 ml of petroleum ether, the precipitate is collected by filtration and washed with 10 ml of petroleum ether. By the above procedure is obtained 1.06 g of 2-chloroacetamidothiazol-4-ylacetyl chloride hydrochloride as colorless crystals.

Elemental analysis, for $C_7H_6Cl_2N_2O_2S \cdot HCl$:
Calcd. C, 29.04; H, 2.44; N, 9.67,
Found C, 28.96; H, 2.24; N, 9.61.

IR spectrum (KBr): 1780 cm$^{-1}$(-COCl)

(2) In 40 ml of tetrahydrofuran is dissolved 1.6 g of the 7-(2-chloroacetamidothiazol-4-yl)acetamido-3-(N-chloroacetyl)carbamoyloxymethyl-3-cephem-4-carboxylic acid obtained in the above (1). To this solution is added 860 mg of thiourea, followed by addition of sodium acetate trihydrate. The mixture is stirred at room temperature overnight. The precipitate is collected by filtration, washed with ethyl ether and dissolved in 10 ml of water. The solution is brought to pH 7 with sodium hydrogen carbonate and purified by column chromatography on Amberlite XAD-2. By the above procedure is obtained 152 mg of sodium 7-(2-aminothiazol-4-yl)acetamido-3-carbamoyloxymethyl-3-cephem-4-carboxylate as white powder.

Elemental analysis, for C$_{14}$H$_{14}$N$_5$O$_6$S$_2$Na.2H$_2$O:
Calcd. C, 35.67; H, 3.85; N, 14.85,
Found C, 35.97; H, 3.88; N, 14.64.
NMR spectrum (60 MHz, in D$_2$O):

3.52 ppm(2H, quartet, 2-CH$_2$), 3.61 ppm(2H, singlet,

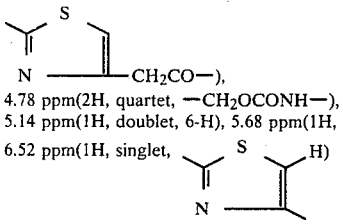
4.78 ppm(2H, quartet, —CH$_2$OCONH—),
5.14 ppm(1H, doublet, 6-H), 5.68 ppm(1H, doublet, 7-H), 6.52 ppm(1H, singlet, 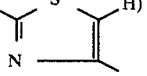)

EXAMPLE 1

(1) In 6 ml of N,N-dimethylacetamide is dissolved 290 mg of 7-amino-3-(N-chloroacetyl)carbamoyloxymethyl-3-cephem-4-carboxylic acid and, under ice-cooling, 276 mg of 2-(2-chloroacetamidothiazol-4-yl)-2-(syn)-methoxyiminoacetyl chloride hydrochloride is added. The mixture is stirred under ice-cooling for 15 minutes and at room temperature for 2 hours. Thereafter, the reaction mixture is diluted with 30 ml of water and extracted twice with 50 ml portions of ethyl acetate. The extracts are pooled, washed with 50 ml of a saturated aqueous solution of sodium chloride and dried over anhydrous magnesium sulfate. The ethyl acetate is distilled off to obtain 402 mg of 7-[2-(2-chloroacetamidothiazol-4-yl)-2-(syn)-methoxyimino]-acetamido-3-(N-chloroacetyl)carbamoyloxymethyl-3-cephem-4-carboxylic acid as a viscous oil.

NMR spectrum (60 MHz, in CDCl$_3$): 3.50 ppm(2H, quartet, 2—CH$_2$), 3.99 ppm(3H, singlet, NOCH$_3$), 4.04, 4.30 ppm(2H×2, singlet×2, ClCH$_2$CO×2), 5.10 ppm(1H, doublet, 6-H), 5.73 ppm(1H, doublet, 7-H), 7.32 ppm(1H, singlet, thiazole, 5-H)

(2) The entire amount of the above product is dissolved in 9 ml of tetrahydrofuran, followed by addition of 168 mg of thiourea and 300 mg of sodium acetate trihydrate. The mixture is stirred at room temperature for 4 hours. The precipitate is collected by filtration, washed with ether and dissolved in 5 ml of water. The solution is adjusted to pH about 7 with sodium hydrogen carbonate and purified by column chromatography on Amberlite XAD-2. By the above procedure is obtained 58 mg of sodium 7-[2-(2-aminothiazol-4-yl)-2-(syn)-methoxyiminoacetamido]-3-carbamoyloxymethyl-3-cephem-4-carboxylate as white powder.

Elemental analysis, for C$_{15}$H$_{15}$N$_6$O$_7$S$_2$Na.3H$_2$O:
Calcd. C, 33.84; H, 3.98; N, 15.78,
Found C, 33.94; H, 3.82; N, 15.42.
NMR spectrum (60 MHz, in D$_2$O): 3.47 ppm(2H, quartet, 2—CH$_2$), 3.92 ppm(3H, singlet, =NOCH$_3$), 4.68 ppm(2H, quartet, —CH$_2$OCONH$_2$), 5.27 ppm(1H, doublet, 6-H), 5.72 ppm(1H, doublet, 7-H), 6.95 ppm(1H, singlet, thiazole 5-H)

Method for production of 2-(2-chloroacetamidothiazol-4-yl)-2-(syn)-methoxyiminoacetyl chloride.

In 5 ml of methylene chloride is suspended 278 mg of the 2-(2-chloroacetamidothiazol-4-yl)-2-(syn)-methoxyiminoacetic acid obtained in Reference Example 6, and, under ice-cooling, 208 mg of phosphorus pentachloride is added. The mixture is stirred at room temperature for 30 minutes, after which it is washed with petroleum ether. By the above procedure is obtained 276 mg of 2-(2-chloroacetamidothiazol-4-yl)-2-(syn)-methoxyiminoacetyl chloride as powders.

Elemental analysis, for C$_8$H$_7$N$_3$O$_3$SCl$_2$.HCl:
Calcd. C, 28.89; H, 2.42; N, 12.63,
Found C, 28.47; H, 2.73; N, 12.12.

EXAMPLE 2

In 22 ml of dry tetrahydrofuran is dissolved 500 mg of the 2-(2-chloroacetamidothiazol-4-yl)-2-(syn)-methoxyiminoacetic acid and, under stirring, 182 mg of triethylamine is added. This mixture is cooled to −10° C. and 245 mg of isobutyl chloroformate is added dropwise. The mixture is stirred at that temperature for 2 hours. To the resultant solution of mixed acid anhydride is added 182 mg of triethylamine together with a solution (ice-cooled) of 590 mg of 7-amino-3-(1-methyl-1H-tetrazol-5-yl)thiomethyl-3-cephem-4-carboxylic acid in 18 ml of a 50% aqueous tetrahydrofuran. The mixture is stirred under ice-cooling for 1 hour and at room temperature for 2 hours. Thereafter, most of the tetrahydrofuran is distilled off under reduced pressure and the residue is diluted with 100 ml of water and with 40 ml of ethyl acetate. Then, under stirring, the aqueous layer is adjusted to pH about 2 with 1 N-HCl. The layers are separated and the water layer is extracted with 60 ml of ethyl acetate. The ethyl acetate layers are pooled, washed with 50 ml of a saturated aqueous solution of sodium chloride and dried. The ethyl acetate is distilled off to obtain 700 mg of 7-[2-(2-chloroacetamidothiazol-4-yl)-2-(syn)-methoxyiminoacetamido]-3-(1-methyl-1H-tetrazol-4-yl)thiomethyl-3-cephem-4-carboxylic acid as a viscous oil.

(2) The entire amount of the above product is dissolved in 15 ml of tetrahydrofuran, followed by the addition of 226 mg of thiourea and 406 mg of sodium acetate trihydrate. The mixture is stirred at room temperature for 4 hours. After the reaction, the precipitate is collected by filtration, washed with ether and dissolved in 10 m of water. The solution is adjusted to pH about 7.0 with sodium hydrogen carbonate and purified by column chromatography on Amberlite XAD-2. By the above procedure is obtained 125 mg of sodium 7-[2-(2-aminothiazol-4-yl)-2-(syn)-methoxyiminoacetamido]-3-(1-methyl-1H-tetrazol-4-yl)thiomethyl-3-cephem-4-carboxylate as white powder.

Elemental analysis, for C$_{16}$H$_{16}$N$_9$O$_5$S$_3$Na.2H$_2$O
Calcd. C, 33.74; H, 3.54; N, 22.13,
Found C, 34.18; H, 3.57; N, 21.79.
NMR spectrum (60 MHz, in D$_2$O): 3.59 ppm(2H, quartet, 2—CH$_2$), 3.93 ppm(3H, singlet, =NOCH$_3$), 3.98 ppm(3H, singlet, N—CH$_3$), 4.08 ppm(2H, quartet, 3—CH$_2$), 5.12 ppm(1H, doublet, 6-H), 5.72 ppm(1H, doublet, 7-H), 6.93 ppm(1H, singlet, thiazole 5-H)

EXAMPLE 3

(1) In 15 ml of N,N-dimethylacetamide is dissolved 762 mg of 7-aminocephalosporanic acid and, under ice-cooling, 931 mg of 2-(2-chloroacetamidothiazol-4-yl)-2-methoxyiminoacetyl chloride hydrochloride (prepared from synisomer) is added. The mixture is stirred under ice-cooling for 15 minutes and at room temperature for 2 hours. The reaction mixture is diluted with 10 ml of water and extracted with 100 ml portions of ethyl acetate. The extracts are pooled, washed with 100 ml of a saturated aqueous solution of sodium chloride and dried. The ethyl acetate is distilled off to obtain 1.4 g of 7-[2-(2-chloroacetamidothiazol-4-yl)-2-(syn)-methoxyiminoacetamido]cephalosporanic acid as an oil.

(2) In 30 ml of tetrahydrofuran is dissolved the entire amount of the above product, followed by the addition of 500 mg of thiourea and, then, of 895 mg of sodium acetate trihydrate. The mixture is stirred at room temperature for 4 hours. The resultant precipitate is collected by filtration, washed with ether and dissolved in 6 ml of water. The solution is adjusted to pH about 7.0 with sodium hydrogen carbonate and purified by means of column chromatography on Amberlite XAD-2. By the above procedure is obtained 78 mg of sodium 7-[2-(2-aminothiazol-4-yl)-2-(syn)-methoxyiminoacetamido]cephalosporanate as white powder.

Elemental analysis, for $C_{16}H_{16}N_5O_7S_2Na.2.5H_2O$:
Calcd. C, 36.78; H, 4.05; N, 13.40,
Found C, 36.93; H, 3.80; N, 12.68.

NMR spectrum (60 MHz, in $D_2O$): 2.07 ppm(3H, singlet, $COCH_3$), 3.53 ppm(2H, quartet, 2—$CH_2$), 3.98 ppm(3H, singlet, $=NOCH_3$), 4.75 ppm(2H, quartet, 3—$CH_2$), 5.21 ppm(1H, doublet, 6-H), 5.81(1H, doublet, 7-H), 7.01 ppm(1H, singlet, thiazole 5-H)

EXAMPLE 4

To 10 ml of water are added 1 g of the sodium 7-[2-(2-aminothiazol-4-yl)-2-(syn)-methoxyiminoacetamido]cephalosporanate obtained in Example 3, 270 mg of 2-methyl-1,3,4-oxadiazole-5-thiol potassium salt and 7 mg of triethylbenzylammonium bromide. The mixture is stirred in nitrogen gas streams at 60° C. for 6 hours. After cooling, the reaction mixture is purified by means of column chromatography on Amberlite XAD-2. By the above procedure is obtained 110 mg of sodium 7-[2-(2-aminothiazol-4-yl)-2-(syn)-methoxyiminoacetamido]-3-(2-methyl-1,3,4-oxadiazol-5-yl)thiomethyl-3-cephem-4-carboxylate as white powder.

Elemental analysis, for $C_{17}H_{16}N_7O_6S_3Na.2H_2O$:
Calcd. C, 35.85; H, 3.54; N, 17.21,
Found C, 35.73; H, 3.72; N, 17.01.

NMR spectrum (60 MHz, in $D_2O$): 8.42 ppm(3H, singlet, oxadiazole 2—$CH_3$), 3.55 ppm(2H, quartet, 2—$CH_2$), 4.02 ppm(3H, singlet, $=NOCH_3$), 5.13 ppm(1H, doublet, 6-H), 5.73 ppm(1H, doublet, 7-H), 6.97 ppm(1H, singlet, thiazole 5-H)

EXAMPLE 5

(1) To 10 ml of tetrahydrofuran are added 833 mg of 2-(2-chloroacetamidothiazol-4-yl)-2-(syn)-methoxyiminoacetic acid, 380 mg of N-hydroxysuccinimide and 630 mg of dicyclohexylcarbodiimide and the mixture is stirred at room temperature for 45 minutes. The precipitate is filtered off and the filtrate is cooled to 5° C. It is then added to a mixed solution of 650 mg 7-aminodesacetoxycephalosporanic acid and 2 ml bis(trimethylsilyl)acetamide in methylene chloride, which has been previously cooled. The mixture is stirred at room temperature overnight and, then, the solvent is distilled off under reduced pressure. To the resultant oil is added 50 ml of water together with 50 ml of ethyl acetate, and the mixture is adjusted to pH about 2.5 with 1 N-hydrochloric acid. The two layers are separated, followed by extractions with two 50 ml portions of ethyl acetate. The ethyl acetate layers are pooled, washed with water and dried. The ethyl acetate is then distilled off to obtain 1.1 g of 7-[2-(2-chloroacetamidothiazol-4-yl)-2-(syn)-methoxyiminoacetamido)-desacetoxycephalosporanic acid as an oil.

(2) The entire amount of the above product is dissolved in 25 ml of tetrahydrofuran, followed by the addition of thiourea and, then, of 632 mg of sodium acetate trihydrate. The mixture is stirred at room temperature for 4 hours. The precipitate is collected by filtration, washed with ether and dissolved in 10 ml of water. The solution is adjusted to pH about 7.0 with sodium hydrogen carbonate and purified by means of column chromatography on Amberlite XAD-2. By the above procedure is obtained 120 mg of sodium 7-[2-(2-aminothiazol-4-yl)-2-(syn)-methoxyiminoacetamido]-desacetoxycephalosporanate as white powders.

Elemental analysis, for $C_{14}H_{14}N_5O_5S_2Na.1.5H_2O$:
Calcd. C, 37.67; H, 3.84; N, 15.68,
Found C, 37.37; H, 3.98; N, 15.38.

NMR spectrum (60 MHz, in $D_2O$) δ: 1.94 ppm(3H, singlet, 3—$CH_3$), 3.46 ppm(2H, quartet, 2-$CH_2$), 4.00 ppm(3H, singlet, $=NOCH_3$), 5.17 ppm(1H, doublet, 6-H), 5.76 ppm(1H, doublet, 7-H), 6.99 ppm(1H, singlet, thiazole 5-H)

The minimal inhibitory concentrations (μg/ml) of some of the compounds according to the above Examples are as follows.

| | Compound | | | |
|---|---|---|---|---|
| Microorganism | Compound of Ex. 1 | Compound of Ex. 3 | Compound of Ex. 2 | Compound of Ex. 5 |
| E. coli NIHJ | 0.10 | 0.20 | 0.10 | 0.78 |
| E. coli 0-111 | 0.024 | 0.05 | 0.024 | 0.39 |
| E. coli T-7 | 0.39 | 0.78 | 0.78 | 6.25 |
| K. pneumonia DT | <0.012 | 0.024 | 0.024 | 0.20 |
| K. pneumonia GN 3835 | 0.05 | 0.05 | 0.20 | 0.20 |
| Ps. aeruginosa Pd 1 | 50 | 25 | 12.5 | >100 |
| Ps. aeruginosa PM 3 | 3.13 | 1.56 | 0.78 | 25 |
| Ps. aeruginosa P2 | 25 | 50 | 50 | >100 |
| Ps. aeruginosa GN3407 | >100 | 50 | 50 | >100 |
| Serr. marcescens IFO 12648 | 1.56 | 3.13 | 0.78 | 12.5 |
| Serratia TN 0024 | 0.20 | 0.78 | 0.20 | 1.56 |
| P. vulgaris IFO 3988 | ≦0.02 | 0.024 | 0.024 | 0.20 |
| P. vulgaris GN 4413 | 1.56 | 0.78 | 0.39 | 1.56 |
| P. mirabilis GN 4359 | ≦0.02 | 0.05 | 0.10 | 0.10 |
| P. morganii IFO3168 | 0.39 | 0.20 | 0.05 | 12.5 |
| P. rettgeri 8(TN0336) | ≦0.012 | ≦0.012 | ≦0.012 | ≦0.012 |
| P. rettgeri 8 GN 4733 | 0.05 | 0.20 | 0.20 | 0.10 |
| Ent. cloacae TN1282 | 6.25 | 6.25 | 1.56 | 50 |
| Cit. freundii GN 99 | 0.20 | 0.20 | 0.10 | 3.13 |
| Cit. freundii GN1706 | 0.39 | 0.39 | 0.20 | 6.25 |
| Acinetobacter anitratus TN-1140 | 6.25 | 25 | 25 | 12.5 |

(Note) The following abbreviations are used to denote the microorganisms employed.
E: Escherichia
K: Klebsiella
Ps: Pseudomonas
Serr: Serratia
P: Proteus
Ent: Enterobacter
Cit: Citrobacter

EXAMPLE 6

(1) In 20 ml of dry tetrahydrofuran is dissolved 500 mg of 2-(2-chloroacetamidothiazol-4-yl)-2-(syn)-methoxyiminoacetic acid and, under stirring, 182 mg of triethylamine is added. The mixture is cooled to −10° C., after which 245 mg of isobutyl chloroformate is added dropwise. The mixture is stirred at that temperature for 2 hours. To the resultant mixture acid anhydride solution is added a solution (ice-cooled) of 180 mg of triethylamine and 492 mg 7-amino-3-carbamoyloxymethyl-3-cephem-4-carboxylic acid in a 50% aqueous tetrahydrofuran. The mixture is stirred under ice-cooling for 1 hour and, then, at room temperature for 2 hours. Most of the tetrahydrofuran is distilled off under reduced pressure, and 100 ml of water and 40 ml of ethyl acetate are added to the residue. The mixture is adjusted to pH about 2 with 1 N-hydrochloric acid. The two layers are separated and the water layer is extracted twice with 50 ml portions of ethyl acetate. The ethyl acetate layers are pooled, washed with water, dried and concentrated. By the above procedure is obtained 650 mg of 7-[2-(2-chloroacetamidothiazol-4-yl)-2-(syn)-methoxyiminoacetamido]-3-carbamoyloxymethyl-3-cephem-4-carboxylic acid as an oil.

(2) The entire amount of the above product is dissolved in 15 ml of tetrahydrofuran, followed by the addition of 226 mg of thiourea and 406 mg of sodium acetate trihydrate. The mixture is stirred at room temperature for 4 hours. The precipitate is collected by filtration, dissolved in 10 ml of water, adjusted to pH about 7 with sodium hydrogen carbonate and purified by column chromatography on Amberlite XAD-2. By the above procedure is obtained 120 mg of sodium 7-[2-(2-aminothiazol-4-yl)-2-(syn)-methoxyiminoacetamido]-3-carbamoyloxymethyl-3-cephem-4-carboxylate as white powders. In NMR spectrum and other properties, this product is found to be identical with the product obtained in Example 1.

EXAMPLE 7

(1) In 45 ml of dry tetrahydrofuran is dissolved 1.11 g of 2-(2-chloroacetamidothiazol-4-yl)-2-(syn)-methoxyiminoacetic acid and, under stirring, 815 mg of tri-n-butylamine is added. The mixture is cooled to −10° C. and 544 mg of isobutyl chloroformate is added dropwise. The mixture is stirred at −10° C. for 2 hours, after which a cold solution of 741 mg tri-n-butylamine and 1.4 g 7-amino-3-(N-chloroacetyl)carbamoyloxymethyl-3-cephem-4-carboxylic acid in 40 ml of a 50% aqueous tetrahydrofuran is added. The mixture is stirred under ice-cooling for 1 hour and at room temperature for 2 hours. Most of the tetrahydrofuran is distilled off under reduced pressure and the residue is diluted with 25 ml of water and washed with 40 ml of ethyl acetate. The water layer is taken and, following addition of 50 ml of ethyl acetate, it is adjusted to pH about 2.5 with 1 N-hydrochloric acid. The mixture is separated into two layers. The water layer is further extracted twice with 50 ml portions of ethyl acetate. The extracts are pooled, washed with 100 ml of a saturated aqueous solution of sodium chloride, dried and finally concentrated. By the above procedure is obtained 1 g of 7-[2-(2-chloroacetamidothiazol-4-yl)-2-(syn)-methoxyiminoacetamido]-3-(N-chloroacetyl)carbamoyloxymethyl-3-cephem-4-carboxylic acid as an oil.

(2) The entire amount of the above product is dissolved in 22 ml of tetrahydrofuran, followed by the addition of 499 mg of thiourea and then, of 892 mg of sodium acetate trihydrate. The mixture is stirred at room temperature for 4 hours. The precipitate is collected by filtration, washed with ether and dissolved in 10 ml of water. The solution is adjusted to pH about 7 with sodium hydrogen carbonate and purified by means of column chromatography on Amberlite XAD-2. By the above procedure is obtained 153 mg of sodium 7-[2-(2-aminothiazol-4-yl)-2-(syn)-methoxyiminoacetamido]-3-carbamoyloxymethyl-3-cephem-4-carboxylate as white powders. Based on NMR and other data, this product is identical with the compound obtained in Example 1.

EXAMPLE 8

In 20 ml of tetrahydrofuran are dissolved 277 mg of 2-(2-chloroacetamidothiazol-4-yl)-2-(syn)-methoxyiminoacetic acid and 270 mg of t-butyl 7-aminodesacetoxycephalosporanic acid, followed by the addition of 206 mg of dicyclohexylcarbodiimide. The mixture is reacted under stirring at room temperature for 6 hours. The precipitated urea derivative is filtered off and the filtrate is poured in 50 ml of water and extracted with ethyl acetate. The ethyl acetate layer is washed with 0.5 N-hydrochloric acid, water and a saturated aqueous solution of sodium chloride in the order mentioned, dried and finally concentrated. By the above procedure is obtained 320 mg of t-butyl 7-[2-(2-chloroacetamidothiazol-4-yl)-2-(syn)-methoxyiminoacetamido]desacetoxycephalosporanate as an oil.

NMR spectrum (60 MHz, in CDCl$_3$): 1.53 ppm(9H, singlet, t-C$_4$H$_9$), 2.13 ppm(3H, singlet, 3—CH$_3$), 3.39 ppm(2H, quartet, 2—CH$_2$), 4.06 ppm(3H, singlet, =NOCH$_3$), 4.29 ppm(2H, singlet, ClCH$_2$CO). 5.06 ppm(1H, doublet, 6-H), 5.86 ppm(1 H, doublet of doublet, 7-H), 7.20 ppm(1H, singlet, thiazole 5-H), 8.14 ppm(1H, doublet, 7—CONH)

(2) The entire amount of the above product is dissolved in 12 ml of tetrahydrofuran, followed by the addition of 100 mg thiourea and 200 mg sodium acetate trihydrate. The mixture is stirred at room temperature for 8 hours. The reaction mixture is diluted with 30 ml of water and extracted with ethyl acetate. The ethyl acetate layer is washed with water, dried and concentrated. The resultant oil is purified by chromatography on silica gel. By the above procedure is obtained 128 mg of t-butyl 7-[2-(2-aminothiazol-4-yl)-2-(syn)-methoxyiminoacetamido]desacetoxycephalosporanate as powders.

NMR spectrum (60 MHz, in CDCl$_3$): 1.52 ppm(9H, singlet, t-C$_4$H$_9$), 2.10 ppm(3H, singlet, 3—CH$_3$), 3.40 ppm(2H, quartet, 2—CH$_2$), 4.00 ppm(3H, singlet, =NOCH$_3$), 5.05 ppm(1H, doublet, 6-H), 5.98 ppm(1H, doublet of doublet, 7-H), 6.66 ppm(1H, singlet, thiazole 5-H), 8.28 ppm(1H, doublet, 7—CONH)

(3) The entire amount of the above product is dissolved in a mixture of 1 ml trifluoroacetic acid and 0.1 ml anisole and the solution is stirred at room temperature for 1.5 hours, after which time ether is added. The resultant precipitate is collected by filtration and washed with ether. By the above procedure is obtained 70 mg of 7-[2-(2-aminothiazol-4-yl)-2-(syn)-methoxyiminoacetamido]-desacetoxycephalosporanic acid trifluoroacetate as powders.

In NMR spectrum (60 MHz, in D$_2$O including NaHCO$_3$), this product is identical with the product obtained in Example 5.

EXAMPLE 9

By the acylation of the 7-amino group of the corresponding cephalosporin compounds in a manner similar to that described in Example 2 (Process A), and by using sodium 7-[2-(2-aminothiazol-4-yl)-2-(syn)-methoxyiminoacetamido]cephalosporanate and heterocyclic thiol compounds in a manner similar to that described in Example 4 (Process B), the following compounds are produced.

(a) Sodium 7-[2-(2-aminothiazol-4-yl)-2-(syn)-methoxyiminoacetamido]-3-(2-methyl-1,3,4-thiadiazol-5-yl)thiomethyl-3-cephem-4-carboxylate (Process B)

NMR spectrum (60 MHz, in D$_2$O): 2.57 ppm(3H, singlet, thiazole 2—CH$_3$), 3.52 ppm(2H, quartet, 2—CH$_2$), 3.95 ppm(3H, singlet, =NOCH$_3$), 5.18 ppm(1H, singlet, 6-H), 5.73 ppm(1H, singlet, 6-H), 5.73 ppm(1H, singlet, 7-H), 6.95 ppm(1H, singlet, thiazole 5-H)

(b) Disodium 7-[2-(2-aminothiazol-4-yl)-2-(syn)-methoxyiminoacetamido]-3-(2-carboxymethyl-1,3,4-thiadiazol-5-yl)thiomethyl-3-cephem-4-carboxylate (Process B)

NMR spectrum (60 MHz, in $D_2O$): 3.56 ppm(2H, quartet, 2—$CH_2$), 3.96 ppm(3H, singlet, =$NOCH_3$), 4.18 ppm(2H, singlet, $CH_2COONa$), 5.20 ppm(1H, doublet, 6-H), 5.74 ppm(1H, doublet, 7-H), 6.97 ppm(1H, singlet, thiazole 5-H)

(c) Sodium 7-[2-(2-aminothiazol-4-yl)-2-(syn)-methoxyiminoacetamido]-3-(1,2,3-triazol-5-yl)thiomethyl-3-cephem-4-carboxylate (Process B)

NMR spectrum (60 MHz, in $D_2O$): 3.57 ppm(2H, quartet, 2—$CH_2$), 3.94 ppm(3H, singlet, =$NOCH_3$), 5.21 ppm(1H, doublet, 6-H), 5.72 ppm(1H, doublet, 7-H), 6.94 ppm(1H, singlet, thiazole 5-H), 7.95 ppm(1H, singlet, triazole 4-H)

(d) Disodium 7-[2-(2-aminothiazol-4-yl)-2-(syn)-methoxyiminoacetamido]-3-(1-carboxymethyl-1,2,3,4-tetrazol-5-yl)thiomethyl-3-cephem-4-carboxylate (Process B)

NMR spectrum (60 MHz, in $D_2O$): 3.55 ppm(2H, quartet, 2—$CH_2$), 3.96 ppm(3H, singlet, =$NOCH_3$), 4.72 ppm

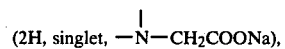

(2H, singlet, —N—$CH_2COONa$), 5.18 ppm(1H, doublet, 6-H), 5.72 ppm(1H, doublet, 7-H), 6.95 ppm(1H, singlet, thiazole 5-H)

(e) 7-[2-(2-Aminothiazol-4-yl)-2-(syn)-methoxyiminoacetamido]-3-[1-(2-N,N-dimethylaminoethyl)-1,2,3,4-tetrazol-5-yl]thiomethyl-3-cephem-4-carboxylic acid betaine (Process A, B)

NMR spectrum (60 MHz, in $D_2O$): 3.01 ppm

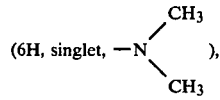

(6H, singlet, —N(CH_3)_2), 3.50 ppm(2H, quartet, 2—$CH_2$), 3.98 ppm(3H, singlet, =$NOCH_3$), 5.18 ppm(1H, doublet, 6-H), 5.74 ppm(1H, doublet, 7-H), 6.96 ppm(1H, singlet, thiazole 5-H)

(f) Sodium 7-[2-(2-aminothiazol-4-yl)-2-(syn)-methoxyiminoacetamido]-3-(6-methyl-1-oxopyridazin-3-yl)thiomethyl-3-cephem-4-carboxylate (Process B)

NMR spectrum (60 MHz, in $D_2O$): 2.60 ppm(3H, singlet, pyridazine 6—$CH_3$), 3.52 (2H, quartet, 2—$CH_2$), 3.98 ppm(3H, singlet, =$NOCH_3$), 5.21 ppm(1H, doublet, 6-H), 5.76 ppm(1H, doublet, 7-H), 6.95 ppm(1H, singlet, thiazole 5-H)

The minimum inhibitory concentration (μg/ml) of some of the obtained compounds as mentioned above are as follows.

| Microorganism | Compound | |
| --- | --- | --- |
| | (a) | (e) |
| E. coli NIHJ | 0.20 | 0.20 |
| E. coli 0-111 | 0.10 | 0.024 |
| E. coli T-7 | 1.56 | 1.56 |
| K. pneumoniae DT | 0.05 | 0.10 |
| K. preumoniae GN 3835 | 0.39 | 0.20 |
| Serr. marcescens IFO 12648 | 0.78 | 1.56 |
| Serratia TN 0024 | 0.78 | 0.78 |

-continued

| Microorganism | Compound | |
| --- | --- | --- |
| | (a) | (e) |
| P. vulgaris IFO 3988 | 0.10 | 0.20 |
| P. vulgaris GN 4413 | 1.56 | 1.56 |
| P. mirabilis GN 4359 | 0.20 | 0.39 |
| P. morganii IFO 3168 | 0.10 | 0.20 |
| P. rettgeri 8(TNO 336) | ≦0.012 | 0.024 |
| P. rettgeri GN 4733 | 0.39 | 0.78 |
| Ent. cloacae IFO12937 | 3.13 | 6.25 |
| Cit. freundii GN 99 | 0.20 | 0.20 |
| Cit. freundii GN 1706 | 0.78 | 0.78 |

EXAMPLE 10

In a mixture of 20 ml water and 10 ml methanol is dissolved 280 mg of sodium carbonate, followed by addition of 477 mg of 7-[2-(2-aminothiazol-4-yl)-2-(syn)-hydroxyiminoacetamido]cephalosporanic acid. To this mixed solution is added 300 mg of dimethyl sulfate dropwise under ice-cooling and stirring. Then, after 25 minutes, 300 mg of potassium carbonate and 300 mg of dimethyl sulfate are added. After another 25 minutes, the reaction mixture is concentrated under reduced pressure and subjected to column chromatography on Amberlite XAD-2, elution being carried out with water. By the above procedure is obtained sodium 7-[2-(2-aminothiazol-4-yl)-2-(syn)-methoxyiminoacetamido]-cephalosporanate. In NMR spectrum, etc., this product is identical with the compound obtained in Example 3.

EXAMPLE 11

(1) To a suspension of 5.54 g of 2-(2-chloroacetamidothiazol-4-yl)-2-(syn)-methoxyiminoacetic acid in 70 ml of methylene chloride is added 2.42 g of triethylamine to obtain solution. Under ice-cooling and stirring, 4.16 g of phosphorus pentachloride is added in a single dose to the above solution. After 5 minutes the ice-bath is removed and the mixture is stirred at room temperature for 20 minutes, after which it is concentrated under reduced pressure. To the residue is added 150 ml of hexane, followed by decantations (twice). After the addition of 90 ml of anhydrous tetrahydrofuran, the precipitated triethylamine hydrochloride is filtered off, whereupon a solution of 2-(2-chloroacetamidothiazol-4-yl)-2-(syn)-methoxyiminoacetyl chloride in tetrahydrofuran is obtained.

On the other hand, to a suspension of 4.28 g of 7-aminodesacetoxycephalosphoranic acid (7-ADCA) in a mixture of 50 ml water and 50 ml tetrahydrofuran is added, under ice-cooling, 4.44 g of triethylamine to prepare a homogeneous solution. Under ice-cooling, the previously prepared acid chloride solution is added dropwise to the above solution over a period of 15 minutes. The mixture is stirred at room temperature for 2 hours, after which a saturated aqueous solution of sodium chloride is added. The mixture is adjusted to pH about 2 with dilute hydrochloric acid and extracted with ethyl acetate. The ethyl acetate layer is washed with a saturated aqueous solution of sodium chloride, dried over magnesium sulfate and concentrated to obtain 8 g of yellowish white powders. The powders are washed with 50 ml of methanol and the insolubles are collected by filtration. By the above procedure is obtained 4.6 g of 7-[2-(2-chloroacetamidothiazol-4-yl)-2-(syn)-methoxyiminoacetamido]desacetoxycephalosporanic acid as white powders.

NMR spectrum (60 MHz, in d$_6$-DMSO): 2.04 ppm(3H, singlet, 3—CH$_3$), 3.50 ppm(2H, broad singlet, 2—CH$_2$), 3.92 ppm(3H, singlet, OCH$_3$), 4.40 ppm(2H, singlet, ClCH$_2$CO), 5.18 ppm(1H, doublet, 6-H), 5.78 ppm(1H, doublet×2, 7-H), 7.50 ppm(1H, singlet, thiazole 5-H).

(2) The above product is reacted and treated in the same manner as Example 5-(2) to obtain sodium 7-[2-(2-aminothiazol-4-yl)-2-(syn)-methoxyiminoacetamido]-desacetoxycephalosporanate as white powders. In NMR spectra and other properties, this product is identical with the product obtained in Example 5.

EXAMPLE 12

In 25 ml of dimethylformamide is suspended sodium 7-[2-(2-aminothiazol-4-yl)-2-(syn)-methoxyiminoacetamido]-desacetoxycephalosporanate and, under ice-cooling, 3.75 g of iodomethyl pivalate is added with 3 ml of dimethylformamide being further added. After 17 minutes, 100 ml of ethyl acetate is added to the reaction mixture and the insolubles are filtered off. The filtrate is washed with water, a 5% aqueous solution of sodium hydrogen carbonate and a saturated aqueous solution of sodium chloride in the order mentioned and dried over magnesium sulfate. The ethyl acetate is then distilled off and the resultant oil (2.4 g) is purified by chromatography on silica gel. By the above procedure is obtained 1 g of pivaloyloxymethyl 7-[2-(2-aminothiazol-4-yl)-2-(syn)-methoxyiminoacetamido]desacetoxycephalosphoranate as white powders.

Elemental analysis, for C$_{20}$H$_{25}$N$_5$O$_7$S$_2$:
Calcd. C, 46.95; H, 4.92; N, 13.69;
Found C, 46.92; H, 4.88; N, 13.13.

NMR spectrum (60 MHz, in CDCl$_3$): 1.24 ppm(9H, singlet, —C(CH$_3$)$_3$), 2.16 ppm, 3.44 ppm(2H, doublet, 2—CH$_2$), 4.10 ppm(3H, singlet, OCH$_3$), 5.16 ppm(1H, doublet, 6-H), 5.94 ppm(2H, singlet, —OCH$_2$O), 6.86 ppm(1H, singlet, thiazole, 5-H)

EXAMPLE 13

0.7 g of the 7-[2-(2-chloroacetamidothiazol-4-yl)-2-(syn)-methoxyiminoacetamido]-desacetoxycephalosporanic acid obtained by the procedure of Example 11-(1) is dissolved in ice-cooled solution of 149 mg of triethylamine in 7 ml of dimethylformamide. Following the addition of 715 mg of iodomethyl pivalate, the mixture is stirred for 15 minutes. To this reaction mixture is added 40 ml of ethyl acetate and the mixture is washed with water, a 5% aqueous solution of sodium hydrogen carbonate and a saturated aqueous solution of sodium chloride in the order mentioned, followed by drying over magnesium sulfate. The ethyl acetate is distilled off to obtain 0.8 g of crude pivaloyloxymethyl 7-[2-(2-chloroacetamidothiazol-4-yl)-2-(syn)-methoxyiminoacetamido]desacetoxycephalosphoranate as a brown oil.

This product is dissolved in 3 ml of dimethylacetamide, followed by the addition of 206 mg of thiourea. The mixture is stirred at room temperature overnight. To this is added 40 ml of ethyl acetate, and the mixture is washed twice with 30 ml portions of a saturated aqueous solution of sodium chloride and dried over magnesium sulfate. The ethyl acetate is distilled off and the resultant brown-colored oil (0.4 g) is purified by chromatography on silica gel. By the above procedure is obtained 0.2 g of pivaloyloxymethyl 7-[2-(2-aminothiazol-4-yl)-2-(syn)-methoxyiminoacetamido]-desacetoxycephalosporanate as white powders.

In NMR spectrum and other properties, this product is identical with the product obtained in Example 12.

EXAMPLE 14

To a suspension of 831 mg of 2-(2-chloroacetamidothiazol-4-yl)-2-(syn)-methoxyiminoacetic acid in 10 ml of methylene chloride are added 360 mg of triethylamine and 624 mg of phosphorus pentachloride. The mixture is stirred at room temperature for 20 minutes, after which 100 ml of hexane is added. The oil that has separated out is obtained by the decantation of the hexane and dissolved in 15 ml of tetrahydrofuran, whereby a solution of 2-(2-chloroacetamidothiazol-4-yl)-2-(syn)-methoxyiminoacetyl chloride is obtained.

On the other hand, 984 mg of 7-amino-3-(1-methyl-1H-tetrazol-5-yl)thiomethyl-3-cephem-4-carboxylic acid and 660 mg of triethylamine are dissolved in 15 ml of a 50% aqueous tetrahydrofuran and, under ice-cooling, the previously prepared acid chloride solution is added dropwise to this solution. The mixture is stirred under ice-cooling for 2 hours, after which the reaction mixture is diluted with water, adjusted to pH about 2 with dilute hydrochloric acid and extracted with ethyl acetate. The ethyl acetate layer is washed with a saturated aqueous solution of sodium chloride and dried over magnesium sulfate. The ethyl acetate is distilled off and the residue is treated with ether. The resultant crystals are collected by filtration. By the above procedure is obtained 1.3 g of 7-[2-(2-chloroacetamidothiazol-4-yl)-2-(syn)-methoxyiminoacetamido]-3-(1-methyl-1H-tetrazol-5-yl)thiomethyl-4-carboxylic acid.

This product is identical with the intermediate obtained by the first part of the process described in Example 2. 5.8 g of the product prepared as above is dissolved in 20 ml of dimethylacetamide and, under ice-cooling, 1.53 g of thiourea is added. The mixture is stirred at room temperature for 15 hours. To this reaction mixture is added 200 ml of ice-water and the pH of the mixture is adjusted to pH 3.5 with sodium hydrogen carbonate. The resultant precipitate is collected by filtration and dissolved in a 10% aqueous solution of sodium hydrogen carbonate. The solution is then passed through a column packed with Amberlite XAD-2. By this purification procedure is obtained 1.58 g of sodium 7-[2-(2-aminothiazol-4-yl)-2-(syn)-methoxyiminoacetamido]-3-(1-methyl-1H-tetrazol-5-yl)thiomethyl-3-cephem-4-carboxylate as white powders.

In NMR spectrum and other properties, this product is identical with the product obtained in Example 2.

EXAMPLE 15

In 10 ml of dimethylformamide is dissolved 1 g of sodium 7-[2-(2-aminothiazol-4-yl)-2-(syn)-methoxyiminoacetamido]-3-(1-methyl-1H-tetrazol-5-yl)thiomethyl-3-cephem-4-carboxylate and, under ice-cooling and stirring, 0.85 g of iodomethyl pivalate is added. The mixture is stirred for 15 minutes. Following the addition of 40 ml of ethyl acetate, the reaction mixture is washed with water, a 5% aqueous solution of sodium hydrogen carbonate and a saturated aqueous solution of sodium chloride in the order mentioned and, then, dried over magnesium sulfate. The ethyl acetate is distilled off under reduced pressure and the residue is dissolved in a small amount of ethyl acetate and filtered. To the filtrate is added ether, followed by cooling. The resultant precipitate is collected by filtration. By the above procedure is obtained 0.4 g of pivaloyloxymethyl 7-[2-(2-aminothiazol-4-yl)-2-(syn)-methoxyiminoacetamido]-3-(1-methyl-1H-tetrazol)-5-yl)thiomethyl-3-cephem-4-carboxylate as white powders.

Elemental analysis, for $C_{22}H_{27}N_9O_7S_3$:
Calcd. C, 42.27; H, 4.34,
Found C, 42.29; H, 4.40.

NMR spectrum (60 MHz, in $CDCl_3$): 1.22 ppm(9H, singlet, —$C(CH_3)_3$), 3.80 ppm(2H, broad singlet), 2—$CH_2$), 3.94, 4.06 ppm(3H×2, singlet×2, N—$CH_3$ & $OCH_3$), 5.94 ppm(2H, singlet, —$OCH_2O$), 5.12 ppm(1H, doublet, 6-H), 6.06 ppm(1H, doublet×2, 7-H), 4.44 ppm(2H, doublet, 3—$CH_2$), 6.81 ppm(1H, singlet, thiazole 5-H).

EXAMPLE 16

In 20 ml of methylene chloride are dissolved 2.776 g of 2-(2-chloroacetamidothiazol-4-yl)-2-(syn)-methoxyiminoacetic acid and 1.2 g of triethylamine, followed by the addition of 2.08 g of phosphorus pentachloride. The mixture is stirred at room temperature for 20 minutes, after which 150 ml of hexane is added. The resultant oily precipitate is separated and dissolved in 20 ml of tetrahydrofuran to prepare a solution of 2-(2-chloroacetamidothiazol-4-yl)-2-(syn)-methoxyiminoacetyl chloride. On the other hand, 3.143 g of 7-amino-3-acetylacetoxymethyl-3-cephem-4-carboxylic acid and 2.20 g of triethylamine are dissolved in 50 ml of a 50% aqueous tetrahydrofuran. To this is added dropwise, under ice-cooling and stirring, the previously prepared acid chloride solution. The mixture is stirred under ice-cooling for 2 hours, after which water is added. The mixture is adjusted to pH 2.0 with dilute hydrochloric acid and extracted with ethyl acetate. The ethyl acetate layer is washed with a saturated aqueous solution of sodium chloride and dried over magnesium sulfate. The ethyl acetate is then distilled off and ether is added to the residue. The resultant crystalline product is collected by filtration. By the above procedure is obtained 4.168 g of 7-[2-(2-chloroacetamidothiazol-4-yl)-2-(syn)-methoxyiminoacetamido]-3-acetylacetoxymethyl-3-cephem-4-carboxylic acid.

NMR spectrum (60 MHz, in $d_6$-DMSO): 2.14 ppm (3H, singlet, —C—$CH_3$),
‖
O 3.60 ppm(4H, broad singlet, —C—$CH_2$—C— & 2-$CH_2$),
‖   ‖
O   O 3.86 ppm(3H, singlet, $OCH_3$), 4.34 ppm(2H, singlet, $ClCH_2CO$), 4.91 ppm(2H, quartet, 3—$CH_2$), 5.13 ppm(1H, doublet, 6-H), 5.80 ppm(1H, doublet×2, 7-H), 7.40 ppm(1H, singlet, thiazole 5-H)

EXAMPLE 17

In 20 ml of dimethylacetamide is dissolved 4.00 g of the 7-[2-(2-chloroacetamidothiazol-4-yl)-2-(syn)-methoxyiminoacetamido]-3-acetylacetoxymethyl-3-cephem-4-carboxylic acid obtained in Example 16, followed by the addition of 1.06 g of thiourea. The mixture is stirred at room temperature for 17 hours, after which 100 ml of ether is added. The oily precipitate is separated and dissolved in a 5% aqueous solution of sodium hydrogen carbonate. The solution is lyophilized and the resultant powdery product is added to 50 ml of methanol. The insolubles are filtered off and the filtrate is added to 300 ml of ether. The precipitate is collected by filtration. By the above procedure is obtained 3.150 g of sodium 7-[(2-(2-aminothiazol-4-yl)-2-(syn)-methoxyiminoacetamido]-3-acetylacetoxymethyl-3-cephem-4-carboxylate.

In 10 ml of water are dissolved 933 mg of the above product, 350 mg of 1-(2-N, N-dimethylaminoethyl)-1H-tetrazol-5-thiol and 168 mg of sodium hydrogen carbonate. The mixture is stirred at 55° C. for 1 hour and, then, the reaction mixture is directly passed through a column packed with Amberlite XAD-2 for purification. By the above procedure is obtained 170 mg of sodium 7-[2-(2-aminothiazol-4-yl)-2-(syn)-methoxyiminoacetamido]-3-[1-(2-N,N-dimethylaminoethyl)-1H-tetrazol-5-yl]thiomethyl-3-cephem-4-carboxylate as white powders. In NMR spectrum and other properties, this product is identical with the product obtained in Example 9.

The following table shows the protective effect ($ED_{50}^*$, mg/kg) of the compounds prepared by the above Examples on infected mice.

TABLE

| Example No. of Sample | Administration | $ED_{50}^*$ (mg/kg) |
|---|---|---|
| 1 | SC | 0.015 (CER : 1.25) |
| 2 | SC | 0.022 (CER : 1.25) |
| 3 | SC | 0.018 (CER : 1.25) |
| 5 | SC | 0.111 (CER : 1.25) |
| 15 | Oral | 0.11 (CEX : 2.51) |
| 17 | Oral | 0.27 (CEX : 2.51) |

*Test animals: male mice (ICR/SLC) 5 mice per group per single dose
Infection: intraperitoneally with *E. coli* 0-111
Observation period: 7 days
( ); control
SC = subcutaneous
CER = cephaloridine

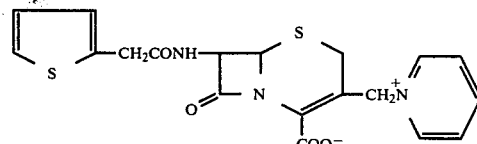

CEX = cephalexin

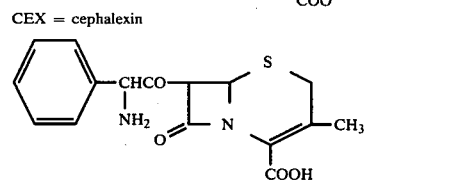

EXAMPLE 18

(1) To a suspension of 55.6 g of 2-(2-chloroacetamidothiazol-4-yl)-2-(syn)-methoxyiminoacetic acid in 600 ml of methylene chloride is added 24.3 g of triethylamine to obtain a solution. Under ice-cooling and stirring, 41.8 g of phosphorus pentachloride is added in two doses to the above solution. After 5 minutes the ice-bath is removed and the mixture is stirred at room temperature for 20 minutes, after which it is concentrated under reduced pressure. To the residue is added 1 l of hexane, followed by decantations (twice). After addition of 600 ml of anhydrous tetrahydrofuran, the precipitated triethylamine hydrochloride is filtered off, whereupon a solution of 2-(2-chloroacetamidothiazol-4-yl)-2-(syn)-methoxyiminoacetyl chloride in tetrahydrofuran is obtained.

On the other hand, to a suspension of 54.7 g of 7-amino-3-carbamoyloxymethyl-3-cephem-4-carboxylic acid in a mixture of 400 ml water and 400 ml tetrahydrofuran is added 61 g of triethylamine under ice-cooling to prepare a homogeneous solution. Under ice-cooling, the previously prepared acid chloride solution is added dropwise to the above solution over a period of 30 minutes. The mixture is stirred at room temperature for 2 hours, after which a saturated aqueous solution of sodium chloride is added. The mixture is adjusted to pH about 2 with dilute hydrochloric acid and extracted with ethyl acetate. The ethyl acetate layer is washed with a saturated aqueous solution of sodium chloride, dried over magnesium sulfate and concentrated to obtain 97.3 g of 7-[2-(2-chloroacetamidothiazol-4-yl)-2-(syn)-methoxyiminoacetamido]-3-carbamoyloxymethyl-3-cephem-4-carboxylic acid. In NMR spectrum and other properties, this product is identical with the product obtained in (1) of Example 6.

NMR spectrum (60 MHz, in $d_6$-DMSO): 3.56 ppm(2H, broad singlet, 2-$CH_2$), 3.93 ppm(3H, singlet, $OCH_3$), 4.35 ppm(2H, singlet, $ClCH_2CO$), 4.78 ppm(2H, quartet, 3—$CH_2$), 5.19 ppm(1H, doublet, 6-H), 5.84 ppm(1H, doublet×2, 7-H), 6.56 ppm(2H, singlet, $OCONH_2$), 7.46 ppm(1H, singlet, thiazole 5-H)

(2) 97.3 g of the product prepared as above (1) is dissolved in 500 ml of N,N-dimethylacetamide and, under ice-cooling, to the solution is added 31.2 g of thiourea. The mixture is stirred at room temperature for 15 hours. To this reaction mixture is added 2 l of ether and then, the oily product is separated. A suspension of this oily product in 300 ml of water is adjusted to pH 7.0 with sodium hydrogen carbonate. Thus obtained solution is passed through a column packed with Amberlite XAD-2. By this purification procedure is obtained 20.2 g of sodium 7-[2-(2-aminothiazol-4-yl)-2-(syn)-methoxyiminoacetamido]-3-carbamoyloxymethyl-3-cephem-4-carboxylate as white powders. In NMR spectrum and other properties, this product is identical with the product obtained in Example 1 or 6.

The structures and properties (IR spectrum) of the compounds (No. 1-33) obtained according to the above processes of this invention are listed in the following table. In this table, IR spectrum (cm$^{-1}$, KBr) means characteristic absorption band due to $\beta$-lactam moiety.

TABLE

[Structure: $R_2NH$-thiazole-C(=N-OCH$_3$)-CONH-β-lactam-cephem with $CH_2R_3$ and COOM substituents]

| Compound No. | $R_2$ | $R_3$ | M | IR (cm$^{-1}$, KBr) |
|---|---|---|---|---|
| 1 | H | -S-(1,3,4-thiadiazol-2-yl) | Na | 1760 |
| 2 | H | -S-(1H-1,2,4-triazol-3-yl) | Na | 1763 |
| 3 | H | -S-(1-methyl-...-N(CH$_3$)...CH$_3$) | Na | 1758 |
| 4 | H | -S-(1-methyl-imidazol-2-yl, N-CH$_3$) | Na | 1760 |
| 5 | H | -S-(4,5-dimethylthiazol-2-yl) | Na | 1763 |
| 6 | H | -S-(5-amino-1,3,4-thiadiazol-2-yl)-NH$_2$ | Na | 1765 |
| 7 | H | -S-(thiadiazolyl)-NHCOOCH$_3$ | Na | 1760 |
| 8 | H | -S-(thiadiazolyl)-CH$_2$CONH$_2$ | Na | 1765 |
| 9 | H | -S-(tetrazol-5-yl, N-CH$_2$CONH$_2$) | Na | 1768 |

TABLE-continued

[Structure: R₂NH-C(=S)-N=C(-CONH-[β-lactam-S])-...=NOCH₃; cephalosporin with CH₂R₃ at 3-position and COOM]

| Compound No. | R₂ | R₃ | M | IR (cm⁻¹, KBr) |
|---|---|---|---|---|
| 10 | H | -S-(4-methyl-5-amino-1,2,4-triazol-3-yl) | Na | 1768 |
| 11 | H | -OH | Na | 1760 |
| 12 | H | -S-(5-((dimethylamino)methyl)-1,3,4-thiadiazol-2-yl) | Na | 1765 |
| 13 | H | -N⁺(pyridinium) | ⊖ | 1765 |
| 14 | H | -N⁺(4-carbamoylpyridinium) | ⊖ | 1765 |
| 15 | H | -S-(5-(SCH₂COONa)-1,3,4-thiadiazol-2-yl) | Na | 1768 |
| 16 | H | -S-(1-(CH₂COONa)-tetrazol-5-yl) | Na | 1765 |
| 17 | H | -S-(1-(CH₂SO₃Na)-tetrazol-5-yl) | Na | 1765 |
| 18 | H | -OCOCH₃ | -CH₂OCOC(CH₃)₃ | 1760 |
| 19 | H | -OCONH₂ | -CH₂OCOC(CH₃)₃ | 1763 |
| 20 | H | -S-(1H-1,2,3-triazol-4-yl) | -CH₂OCOC(CH₃)₃ | 1765 |
| 21 | H | -S-(1-(CH₂CH₂N(CH₃)₂)-tetrazol-5-yl) | -CH₂OCOC(CH₃)₃ | 1768 |
| 22 | H | H | -CH(CH₃)OCOOC₂H₅ | 1760 |
| 23 | H | -OCOCH₃ | -CH(CH₃)OCOOC₂H₅ | 1763 |
| 24 | H | -OCONH₂ | -CH(CH₃)OCOC(CH₃)₃ | 1763 |

TABLE-continued

| Compound No. | R₂ | R₃ | M | IR (cm⁻¹, KBr) |
|---|---|---|---|---|
| 25 | H | -S-(1-methyl-tetrazol-5-yl) | $-\underset{CH_3}{CH}OCOOC_2H_5$ | 1765 |
| 26 | H | -S-(1H-1,2,3-triazol-5-yl) | $-\underset{CH_3}{CH}OCOOC_2H_5$ | 1768 |
| 27 | H | -S-(1-(2-dimethylaminoethyl)tetrazol-5-yl) | $-\underset{CH_3}{CH}OCOC(CH_3)_3$ | 1765 |
| 28 | H | H | phthalidyl | 1760 |
| 29 | H | -OCOCH₃ | phthalidyl | 1763 |
| 30 | H | -OCONH₂ | phthalidyl | 1763 |
| 31 | H | -S-(1-methyl-tetrazol-5-yl) | phthalidyl | 1765 |
| 32 | H | -S-(1H-1,2,3-triazol-5-yl) | phthalidyl | 1763 |
| 33 | H | -S-(1-(2-dimethylaminoethyl)tetrazol-5-yl) | phthalidyl | 1768 |

Injectable composition 250 mg of sodium 7-[2-(2-aminothiazol-4-yl)-2-(syn)-methoxyiminoacetamido]-3-carbamoyloxymethyl-3-cephem-4-carboxylate, or sodium 7-[2-(2-aminothiazol-4-yl)-2-(syn)-methoxyiminoactamido]-3-(1-methyl-1H-tetrazol-5-yl)thiomethyl-3-cephem-4-carboxylate, or sodium 7-[2-(2-aminothiazol-4-yl)-2-(syn)-methoxyiminoactamido]cephalosporanate is dissolved in 1 ml of sterilized water before use.

What we claim is:

1. A member selected from the group consisting of a 7-[2-(2-aminothiazol-4-yl)-2-(syn)-methoxyiminoacetamido]cephalosporin compound of the formula:

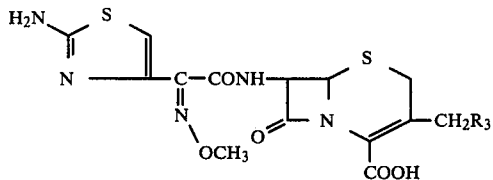

wherein $R_3$ is pyridinium or 4-carbamoylpyridinium, and a pharmaceutically acceptable salt or ester thereof.

2. An antibacterial composition which comprises (a) an antibacterially effective amount of a member selected from the group consisting of a 7-[2-(2-aminothiazol-4-yl)-2-(syn)-methoxyiminoacetamido]cephalosporin compound of the formula:

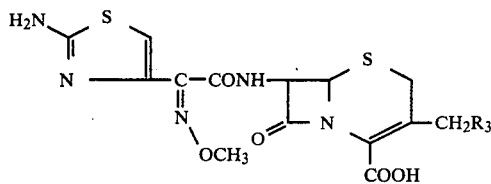

wherein $R_3$ is pyridinium or 4-carbamoylpyridinium, and a pharmaceutically acceptable salt or ester thereof in admixture with (b) a pharmaceutically acceptable excipient or diluent therefor.

3. A compound as claimed in claim 1, wherein the compound is 7-[2-(2-aminothiazol-4-yl)-2-(syn)-methoxyiminoacetamido]-3-pyridiniummethyl-3-cephem-4-carboxylate.

4. A compound as claimed in claim 1, wherein the compound is 7-[2-(2-aminothiazol-4-yl)-2-(syn)-methoxyiminoacetamido]-3-(4-carbamoylpyridinium)methyl-3-cephem-4-carboxylate.

* * * * *